(12) United States Patent
Shi et al.

(10) Patent No.: US 9,210,925 B2
(45) Date of Patent: Dec. 15, 2015

(54) MULTIPOTENT POSTNATAL STEM CELLS FROM HUMAN PERIODONTAL LIGAMENT AND USES THEREOF

(75) Inventors: Songtao Shi, Irvine, CA (US); Byoung-Moo Seo, Seoul (KR); Masako Miura, Kyoto (JP)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 792 days.

(21) Appl. No.: 11/433,627

(22) Filed: May 12, 2006

(65) Prior Publication Data

US 2007/0009492 A1 Jan. 11, 2007

Related U.S. Application Data

(63) Continuation of application No. PCT/US2004/039248, filed on Nov. 22, 2004.

(60) Provisional application No. 60/523,602, filed on Nov. 20, 2003.

(51) Int. Cl.
*A61K 35/32* (2015.01)
*A61C 5/00* (2006.01)
*A01N 1/02* (2006.01)
*A61C 8/02* (2006.01)
*C12N 5/0775* (2010.01)

(52) U.S. Cl.
CPC ............... *A01N 1/02* (2013.01); *A01N 1/0205* (2013.01); *A01N 1/0221* (2013.01); *A61C 8/0006* (2013.01); *A61K 35/32* (2013.01); *C12N 5/0664* (2013.01)

(58) Field of Classification Search
None
See application file for complete search history.

(56) References Cited

U.S. PATENT DOCUMENTS

| 6,361,933 | B1 | 3/2002 | Wiggins et al. | |
| 2003/0113910 | A1* | 6/2003 | Levanduski | 435/325 |
| 2003/0143207 | A1* | 7/2003 | Livesey et al. | 424/93.7 |

OTHER PUBLICATIONS

Saito et al. "A cell line with characteristics of the periodontal ligament fibroblasts is negatively regulated for mineralization and Runx2/Cbfa1/Osf2 activity, part of which can be overcome by bone morphogenetic protein-2" Journal of Cell Science 115 (21) 2002, p. 4191-4200.*
Matsuda et al. "Role of epidermal growth factor and its receptor in mechanical stress-induced differentiation of human periodontal ligament cells in vitro" Archives of Oral Biology 43 (1998) 987±997.*
Tanaka et al.,"Comparison of charcateristics of periodontal ligament cells obtained from outgrowth and enzyme-digested culture methods", Archives of Oral Biology, 2010, pp. 1-9.*
Hirayama et al., "Ultrastructural and cytochemical studies of clonal cell lines in fibroblasts derived from human periodontal ligaments-establishment of clonal cell lines in fibroblasts from periodontal ligaments", Shikwa Gakuho, 1989, vol. 89(12), pp. 1849-54, English abstract.*
Shi et al., "Perivascular Niche of Postnatal Mesenchymal Stem Cells in Human Bone Marrow and Dental Pulp", Journal of Bone and Mineral Research, 2003, vol. 18, No. 4, pp. 696-704.*
Gronthos et al., "Postnatal human dental pulp stem cells (DPSCs) in vitro and in vivo", PNNAS, vol. 97, No. 25, pp. 13625-13630.*
Temmerman et al., "Influence of cryopreservation on human periodontal ligament cells", Cell Tissue Banking, epub May 31, 2007, vol. 9, pp. 11-18.*
International Search Report—PCT/US2004/039248, Authorized Officer—A. Nichogiannopoulou,(Jul. 29, 2005),2.
Beertsen, W. , et al., "The periodontal ligament: a unique, multifunctional connective tissue", *Periodontology 2000*, 13, (Feb. 1997),20-40.
Hoang, A. M., et al., "Development and Characterization of a Transformed Human Periodontal Ligament Cell Line", *Journal of Peridontology*, 68 (11), ISSN: 0022-3492,(Nov. 1997),1054-1062.
Lekic, P. C., et al., "Transplantation of Labeled Periodontal Ligament Cells Promotes Regeneration of Alveolar Bone", *Anatomical Record*, 262 (2), (Feb. 1, 2001),193-202.
Liu, H. W., et al., "A collagenous cementum-derived attachment protein is a marker for progenitors of the mineralized tissue-forming cell lineage of the periodontal ligament", *Journal of Bone & Mineral Research: The Official Journal of American Society for Bone & Mineral Research*, 12 (10), (Oct. 1997),1691-1699.
McCulloch, C. A., "Progenitor cell populations in the periodontal ligament of mice", *The Anat. Record*, 211(3), (Mar. 1985),258-262.
Seo, B. M., et al., "Investigation of multipotent postnatal stem cells from human periodontal ligament", *Lancet The, Lancet Limited*, 364 (9429), (Jul. 10, 2004),149-155.
Huang et al., "Dental Stem Cells and Tooth Banking for Regenerative Medicine," *J. Exp. Clin. Med*. 2(3):111-117 (Jun. 2010).
Hubel, "Parameters of Cell Freezing: Implications for the Cryopreservation of Stem Cells," *Transfusion Medicine Reviews* 11(3):224-233 (Jul. 1997).
Lundell et al., "Clinical Scale Expansion of Cryopreserved Small Volume Whole Bone Marrow Aspirates Produces Sufficient Cells for Clinical Use," *Journal of Hematotherapy* 8:115-127 (Apr. 1999).
Schwartz and Greve, "Cryopreservation before replantation of mature teeth in monkeys," *Int. J. Oral Surgery* 14:350-361 (Aug. 1985).

* cited by examiner

*Primary Examiner* — Laura Schuberg
(74) *Attorney, Agent, or Firm* — Klarquist Sparkman, LLP

(57) ABSTRACT

The invention generally relates to postnatal periodontal ligament stem cells and methods for their use. More specifically, the invention relates in one aspect to postnatal periodontal ligament multipotent stem cells, use of the cells to generate periodontium, differentiation of the cells and methods of tissue cryopreservation.

36 Claims, 6 Drawing Sheets

SEQUENCE LISTING

<160> NUMBER OF SEQ ID NOS: 10

<210> SEQ ID NO 1
<211> LENGTH: 20
<212> TYPE: DNA
<213> ORGANISM: Homo sapiens

<400> SEQUENCE: 1
ctcctattga cccagaaagc                                               20

<210> SEQ ID NO 2
<211> LENGTH: 20
<212> TYPE: DNA
<213> ORGANISM: Homo sapiens

<400> SEQUENCE: 2
gtagagctga gtcttctcag                                               20

<210> SEQ ID NO 3
<211> LENGTH: 21
<212> TYPE: DNA
<213> ORGANISM: Homo sapiens

<400> SEQUENCE: 3
atggagagca aagccctgct c                                             21

<210> SEQ ID NO 4
<211> LENGTH: 21
<212> TYPE: DNA
<213> ORGANISM: Homo sapiens

<400> SEQUENCE: 4
gttaggtcca gctggatcga g                                             21

<210> SEQ ID NO 5
<211> LENGTH: 21
<212> TYPE: DNA
<213> ORGANISM: Homo sapiens

<400> SEQUENCE: 5
agccgcatct tcttttgcgt c                                             21

<210> SEQ ID NO 6
<211> LENGTH: 21
<212> TYPE: DNA
<213> ORGANISM: Homo sapiens

<400> SEQUENCE: 6
tcatatttgg caggtttttc t                                             21

<210> SEQ ID NO 7
<211> LENGTH: 20
<212> TYPE: DNA
<213> ORGANISM: Homo sapiens

<400> SEQUENCE: 7
ctggcctcca gctacatctc                                               20

<210> SEQ ID NO 8
<211> LENGTH: 20
<212> TYPE: DNA
<213> ORGANISM: Homo sapiens

-continued

```
<400> SEQUENCE: 8
ctttctctgg ttgctgaggc                                                  20

<210> SEQ ID NO 9
<211> LENGTH: 19
<212> TYPE: DNA
<213> ORGANISM: Homo sapiens

<400> SEQUENCE: 9
tggctcacgc ctgtaatcc                                                   19

<210> SEQ ID NO 10
<211> LENGTH: 21
<212> TYPE: DNA
<213> ORGANISM: Homo sapiens

<400> SEQUENCE: 10 tttttgaga cggagtctcg c                                                 21
```

MULTIPOTENT POSTNATAL STEM CELLS FROM HUMAN PERIODONTAL LIGAMENT AND USES THEREOF

REFERENCE TO RELATED APPLICATIONS

This application is a continuation under 35 U.S.C. 111(a) of PCT/US2004/039248, filed Nov. 22, 2004 and published as WO 2005/052140 A2, filed Jun. 9, 2005, which claimed priority under 35 U.S.C. 119(e) from U.S. Provisional Application Ser. No. 60/523,602 filed Nov. 20, 2003, which applications and publication are incorporated herein by reference and made a part hereof.

STATEMENT OF GOVERNMENT RIGHTS

This invention was developed with the support of the Department of Health and Human Services. The United States Government may have certain rights in the invention.

FIELD OF THE INVENTION

The invention generally relates to postnatal periodontal ligament stem cells (PDLSCs) and methods for their use. More specifically, the invention relates to PDLSCs, use of the cells for periodontal tissue regeneration for periodontal disease treatment, differentiation of the cells and methods of tissue cryopreservation.

BACKGROUND OF THE INVENTION

Postnatal stem cells (meaning those present after birth) are unspecialized cells that can renew themselves extensively and develop into more mature cells having specialized functions. Stem cells may be induced under certain physiologic or experimental conditions to become cells with special functions, such as the beating cells of the heart muscle, or the insulin-producing cells of the pancreas. The process by which a stem cell becomes a cell with special functions is known as differentiation. Differentiation can be induced through use of multiple signals that can include chemicals secreted by other cells, physical contact with neighboring cells, and certain molecules in the microenvironment. Thus, stem cells can be treated with specific signals to become specific types of cells having useful functions. These newly differentiated cells can then be used to generate replacements for cells that are lost through normal wear and tear, injury, or disease.

Periodontal (gum) diseases, including gingivitis and periodontitis, are serious infections that, left untreated, can lead to tooth loss. In fact, periodontal diseases are a major cause of tooth loss, and are a substantial public health burden. Periodontal diseases are characterized by destruction of periodontium (supporting tissue for tooth (e.g., the gums)) including PDL, cementum, alveolar bone, and ginigiva. Periodontal disease can affect one tooth or many teeth. Many approaches have been developed for treating periodontal defects, including guided tissue regeneration, the use of growth factors, and the use of enamel matrix proteins, but none of these methods provides a consistently predictable outcome. Accordingly, there remains a need to find new methods to treat periodontal diseases.

SUMMARY OF THE INVENTION

Methods and materials are provided by the current invention that address the aforementioned needs. The present invention provides a novel population of postnatal stem cells from human periodontal ligament (PDL), named PDL stem cells (PDLSCs). The invention provides an isolated human postnatal periodontal ligament multipotent stem cell, a method to implant a periodontal cell within an organism, a method to implant an adipocyte within an organism, and a method to generate periodontal tissue, including cementum and periodontal ligament, in vivo and in vitro.

Postnatal periodontal ligament multipotent stem cells can differentiate into collagen fiber forming cells (fibroblasts), cementoblasts, cementocytes, and adipocytes. The stem cells can be obtained from periodontal ligament and can be stored for later use. The periodontal ligament multipotent stem cell can be grown in tissue culture medium. Preferably, the tissue culture medium includes serum. Preferably, the tissue culture medium does not include serum. The tissue culture medium can include one or more growth factors.

The invention also provides methods to generate periodontal tissue, including periodontal ligament and cementum, by implanting a periodontal ligament stem cell or differentiated progeny thereof within a subject. Generally, the method involves implanting a postnatal periodontal ligament multipotent stem cell into a subject. Preferably the subject is a mammal. More preferably the subject is a human. The postnatal periodontal ligament multipotent stem cell may be obtained from one subject and implanted into a different subject. Preferably, the postnatal periodontal ligament multipotent stem cell is obtained from and implanted into the same subject. The postnatal periodontal ligament multipotent stem cell may be expanded ex vivo prior to being implanted into the subject. The postnatal periodontal ligament multipotent stem cell may be induced to differentiate prior to being implanted into the subject. A postnatal periodontal ligament multipotent stem cell that is not in combination with a carrier can be implanted into a subject. A postnatal periodontal ligament multipotent stem cell that is in combination with a carrier can be implanted into a subject. Preferably, the carrier contains hydroxyapatite. More preferably, the carrier contains tricalcium phosphate. Most preferably, the carrier contains hydroxyapatite and tricalcium phosphate. The method of the invention can be used to generate periodontal tissue/cells in response to trauma to the periodontium. Preferably the trauma is erosion of the periodontium. More preferably, the trauma results from periodontal disease.

The invention provides a method to produce adipose tissue within a subject. Generally, the method involves implanting a periodontal ligament stem cell into an organism. Preferably, the periodontal ligament stem cell is a periodontal ligament multipotent stem cell. More preferably, the periodontal ligament stem cell is a human postnatal periodontal ligament multipotent stem cell. Preferably the subject is a mammal. More preferably the subject is a human. The periodontal ligament stem cell may be expanded ex vivo prior to being implanted into the organism. Preferably, the periodontal ligament stem cell is adipogenesis induced prior to being implanted into the subject. A periodontal ligament stem cell that is not in combination with a carrier can be implanted into a subject. A periodontal ligament stem cell that is in combination with a carrier can be implanted into a subject.

The invention also provides a method of cryopreserving tissue from which functional periodontal stem cells can later be isolated by immersing a portion of an isolated periodontal ligament with serum comprising about 1 to about 20% dimethyl sulfoxide and flash freezing the immersed periodontal ligament thereby cryopreserving periodontal stem cells. In a preferred method, the serum includes about 10% DMSO. Preferably the periodontal ligament is mammalian. More preferably the periodontal ligament is a human periodontal ligament. Generally, the cryopreserved tissue is thawed at about 35° to about 39° C. After thawing, the ligament is digested or mechanically disrupted to form a suspension of single cells and the suspension of single cells is seeded into a tissue culture vessel (e.g., a tissue culture flask) in the presence of medium, such as a stem cell medium.

The invention further provides the use of the PDLSCs in medical therapy, including, but not limited to, treating trauma to the periodontium. The invention further provides for the use of PDLSCs to prepare a medicament for the treatment of trauma to the periodontium. The trauma can result from, for example, periodontal disease, a dental procedure or a physical trauma from, for example, an accident.

DETAILED DESCRIPTION OF THE INVENTION

Figure 1:
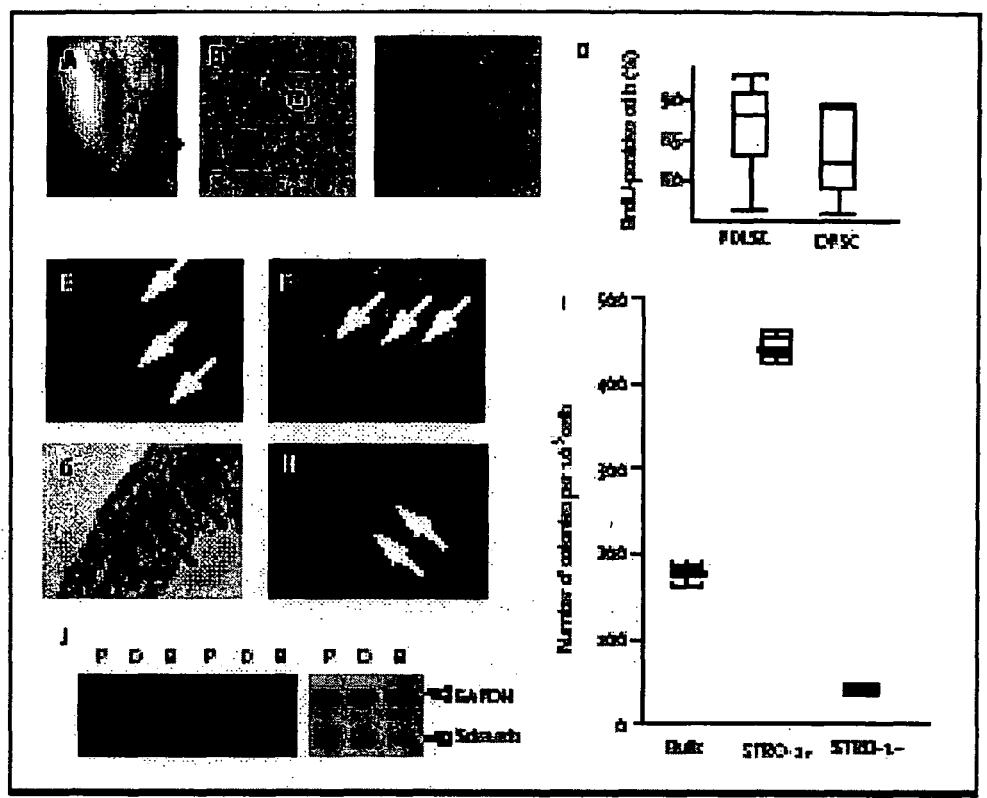
FIG. 1 depicts the isolation of human PDLSCs. (A) Extracted human third molar showing PDL attached to the surface of the roots (arrow). (B) Single colonies formed after PDLSCs were plated at low density and cultured as described below. (C) Cell clusters derived from PDL formed a single colony stained with 0.1% toluidine blue. (D) Bromodeoxyuridine (BrdU) labeling efficiency of PDLSCs and DPSCs were assessed by BrdU incorporation for 24 h. The number of BrdU-positive cells was expressed as a percentage of total number of cells counted from six replicate cultures as shown in boxplot. PDLSCs showed a higher uptake rate than did DPSCs, but there was no significant statistical difference (p=0.294). Horizontal lines are median values. Bars show maximum and minimum values. (E-F) Immunocytochemical staining showed that cultured PDLSCs expressed STRO-1 (E) and CD146/MUC18 (F), two early mesenchymal progenitor markers. (G-H) PDL tissue was positive for STRO-1 antibody with immunohistochemical (G) and fluorescence (H) staining. (I) Freshly isolated single-cell suspensions of human PDL reacted with the STRO-1 antibody after immunoselection with magnetic Dynal beads as described below. Clonogenic assays were subsequently done with unfractionated (bulk), STRO-1 negative (STRO-1−) and STRO-1 positive (STRO-1+) cell fractions. Data obtained from five individual PDL samples are shown in boxplot. Highlighted horizontal lines in boxplots are median values. (J) RT-PCR (left) and northern blot analysis (right) showed that cultured PDLSCs (P) expressed higher levels of scleraxis, a transcription factor specifically expressed in tendon cells, compared with DPSCs (D) and BMSSCs (B). GAPDH=glyceraldehyde phosphate dehydrogenase (control).

The invention includes human postnatal periodontal ligament multipotent stem cells that can give rise to diverse cell types. In a preferred embodiment, the cells are isolated from human tissue. As discussed below, for the first time it is demonstrated that PDL contains postnatal stem cells that are able to differentiate into cementoblasts, cementocytes, adipocytes, and collagen fiber forming cells (fibroblasts). As demonstrated in the Examples below, PDLSCs are capable of forming cementum/PDL structure in vivo. Thus, PDLSCs are useful to generate PDL and cementum for periodontal disease treatment. Additionally, PDLSCs are useful to generate adipocytes for fat formation. Furthermore, PDLSCs may also be useful in the treatment of stroke and bone defects, including fracture and osteoporosis.

Periodontal ligament (PDL) has been characterized as a soft, specialized connective tissue that connects the cementum of the tooth and to the alveolar bone of the maxillary and mandible to maintain teeth in situ, support teeth for function, and preserve tissue homeostasis. PDL has been assumed to be a high turnover tissue with a strong capability for tissue regeneration, while maintaining the space for normal tooth function. As described herein, multipotent stem cells were isolated from human periodontal ligament. The isolated periodontal ligament stem cells (PDLSCs) were found to express mesenchymal stem cell markers, including STRO-1 and MUC18, along with a high level of a tendon specific marker, Scleraxis (SCX). These markers can be used to distinguish PDLSCs from adjacent stem cells, such as dental pulp stem cells (DPSCs) and bone marrow stromal stem cells (BMSSCs).

Stem cells isolated from periodontal ligament are capable of differentiating into a variety of cell types. These cell types include cementoblasts, cementocytes, adipocytes, and fibroblasts. Periodontal ligament stem cells were also found to be able to generate periodontal tissue. For example, when transplanted into immunocompromised mice, PDLSCs generated a cementum-like structure along with a periodontal ligament-like connective tissue. Thus, the present invention provides a method for stem cell-mediated tissue regeneration to repair injury to the periodontal region including injury resulting from periodontal diseases (characterized by the destruction of the periodontium (support tissue for the tooth)), such as periodontitis, a chronic infection of periodontal ligament and adjacent tissues.

As described herein, periodontal ligament multipotent stem cells represent a novel population of postnatal stem cells capable of extensive proliferation and multi-potential differentiation, including differentiation into cementoblasts, cementocytes, adipocytes, and fibroblasts. Periodontal ligament may, therefore, be an ideal resource of stem cells to repair damaged periodontal tissue or to create fat when needed.

The invention therefore includes methods to generate periodontal tissue. The method involves transplanting periodontal ligament stem cells into a subject. Preferably the subject is a mammal. More preferably the subject is a human. The periodontal ligament stem cells can be human postnatal periodontal ligament multipotent stem cells. Preferably, the periodontal ligament stem cells (PDLSCs) express mesenchymal stem cell markers, including STRO-1 and MUC18, along with a high level of a tendon specific marker, Scleraxis (SCX).

The newly discovered ability to generate reparative periodontal tissue represents a great technical advance because it provides for the restorative generation of lost periodontium, i.e., cementum, alveolar bone, and periodontal ligament. This in turn has great practical value because it allows a dental or medical practitioner to provide better care to a patient in need of such treatment. For example, current protocol for the treatment of periodontal disease involves the use of surgery to repair the trauma. This can lead to pain, and may require a patient to undergo further painful treatment and incur additional cost. Application of the methods of the invention to a subject in need of treatment for periodontal disease, or other injury to the periodontium, allows the periodontal ligament stem cells to be placed into the traumatized region by a minimally invasive procedure to produce regenerative periodontal tissue. Thus, it is thought that use of the method of the invention can reduce costs and pain associated with dental treatment.

One embodiment of the invention provides for the cryopreservation of human tissue and recovery of functional stem cells (e.g., mesenchymal) from cryopreserved human tissue (e.g., periodontal ligament or bone stromal tissue). Thereby providing a practical approach to preserving tissues, such as human tissue, for subsequent postnatal stem cell isolation and tissue regeneration.

DEFINITIONS

Abbreviations: Periodontal ligament (PDL), Periodontal ligament stem cell (PDLSC), Scleraxis (SCX), Stem cells from human exfoliated deciduous teeth (SHED), Bone marrow stromal stem cell (BMSSC), Dental pulp stem cell from a permanent tooth (DPSC), phosphate buffered saline (PBS), bone morphogenetic protein-4 (BMP-4), dentin sialoprotein (DSP), vascular endothelial growth factor (VEGF), basic fibroblast growth factor (bFGF), epidermal growth factor (EGF), alkaline phosphatase (ALP), matrix extracellular phosphoglycoprotein (MEPE), glutamic acid decarboxylase (GAD).

"Postnatal" refers to any time of or occurring after birth, including immediately after birth and any time thereafter. However, the invention is not limited to postnatal stem cells and may be practiced with other stem cells, including embryonic stem cells.

As used herein, "stem cell" refers to a relatively undifferentiated cell that can be induced to proliferate and that can produce progeny that subsequently differentiate into one or more mature cell types. In many biological instances, stem cells are "multipotent" because they can produce progeny of more than one distinct cell type, but this is not required for "stem-ness." Self-renewal is the other classical part of the stem cell definition. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Additionally, it is possible that cells that begin as stem cells might proceed toward a differentiated phenotype, but then "reverse" and re-express the stem cell phenotype.

As used herein, "differentiation" refers to the developmental process whereby cells assume a specialized phenotype, i.e., acquire one or more characteristics or functions distinct from other cell types.

The terms "implant" and "transplant" are interchangeable and refer to a graft or insert of tissue or a cell(s) within a subject. The tissue or cell can come from the same subject in which the cell or tissue is being transplanted or it can originate from a different subject (e.g., tissue or cell transplanted from a donor to a recipient; in some cases the subject can be both donor and recipient).

The term "carrier" refers to a vehicle with which a stem cell can be mixed prior to being implanted into a subject. Examples of carriers include, but are not limited to, gelatin, polyvinyl sponges, collagen matrices, and hydroxyapatite/tricalcium phosphate ceramics. Carriers can be prepared in numerous forms. For example, carriers can be formed into blocks, powders, strips, and the like. Carriers are known in the art and have been described (Krebsbach et al., *Transplantation*, 63:1059 (1997)).

A "periodontal ligament stem cell" refers to a postnatal stem cell that is isolated from the periodontal ligament. A "human postnatal periodontal ligament multipotent stem cell" refers to a stem cell that is isolated from human periodontal ligament.

The term "isolated" means that a cell of the invention is not in the state found in nature. For example, the cell is free of one or more contaminants or one or more cell types with which a cell of the invention is naturally found. Moreover, an isolated cell of the invention may be present in a form that is sufficiently pure to be used therapeutically or for research. The term isolated does not require a cell of the invention to be free of all contaminants.

"Expansion" refers to the propagation of a cell or cells without differentiation.

A "recipient cell" is a cell within a subject that becomes proximate to a stem cell when the stem cell is implanted into the subject. A recipient cell may be in direct contact with an implanted stem cell, or not in direct contact with the implanted cell but still influenced by the implanted cell. For example, an implanted human postnatal periodontal ligament multipotent stem cell may cause a recipient cell to form cementum without actually contacting the recipient cell.

The term "trauma" refers to an event that causes a cell to undergo a detrimental change. Examples of trauma include, physical injury resulting from accident or medical treatment, including surgery, disease (e.g., periodontal disease), degeneration, and the like.

As used herein, "subject" refers to any vertebrate, preferably a mammal, more preferably a human. Mammals include, but are not limited to, humans, farm animals, sport animals, and pets.

As used herein, "treat" or "treating" includes treating, preventing, ameliorating, or inhibiting physical or disease related damage and/or a symptom of physical or disease related damage of a subject.

As used herein, an "effective amount" generally means an amount which provides the desired local or systemic effect and performance. For example, an effective dose is an amount sufficient to affect a beneficial or desired clinical result.

The terms "comprises," "comprising," and the like can have the meaning ascribed to them in U.S. Patent Law and can mean "includes," "including" and the like. As used herein, "including" or "includes" or the like means including, without limitation.

I. An Isolated Human Postnatal Periodontal Ligament Multipotent Stem Cell

The Invention Provides Isolated Postnatal Periodontal Ligament multipotent stem cells. These cells and methods to isolate them are disclosed in detail herein.

A. Culture of PDLSCs

PDLSCs can be maintained and allowed to expand in culture medium that is well established in the art and commercially available from the American Type Culture Collection (ATCC). Such media include, but are not limited to Dulbecco's Modified Eagle's Medium® (DMEM), DMEM F12 Medium®, Eagle's Minimum Essential Medium®, F-12K Medium®, Iscove's Modified Dulbecco's Medium®, RPMI-1640 Medium®.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements, and bovine embryonic fluid. Sera can be heat-inactivated at 55-65° C. if deemed necessary to inactivate components of the complement cascade.

Additional supplements can also be used to supply the cells with trace elements for optimal growth and expansion. Such supplements include insulin, transferrin, sodium selenium and combinations thereof. These components can be included in a salt solution such as, but not limited to Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids, however some require supplementation prior to culturing cells. Such amino acids include, but are not limited to L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine.

Cytokines, growth factors and/or differentiation factors can also be used in cell culture, including, but not limited to stromal cell derived factor-1 (SDF-1), stem cell factor (SCF), angiopoietin-1, placenta-derived growth factor (PIGF), granulocyte-colony stimulating factor (G-CSF), any agent which promotes the expression of endothelial adhesion molecules, such as ICAMs and VCAMs, any agent which facilitates the homing process, vascular endothelial growth factor (VEGF), fibroblast growth factors (e.g., FGF4, FGF8, bFGF), Wnt11, DKK1, ascorbic acid, isoproterenol, endothelin, any agent which promotes angiogenesis, including VEGF, aFGF, angiogenin, angiotensin-1 and -2, betacellulin, bFGF, Factor X and Xa, HB-EGF, PDGF, angiomodulin, angiotropin, angiopoietin-1, prostaglandin E1 and E2, steroids, heparin, 1-butyryl-glycerol, and nicotinic amide, any agent which decreases apoptosis including, but not limited to, β-blockers, angiotensin-converting enzyme inhibitors (ACE inhibitors), carvedilol, angiotensin II type 1 receptor antagonists, caspase inhibitors, cariporide, eniporide or a combination thereof.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others.

Also contemplated is the use of feeder cell layers. Feeder cells are used to support the growth of cultured cells, including stem cells. Feeder cells are normal cells that have been inactivated by γ-irradiation. In culture, the feeder layer serves as a basal layer for other cells and supplies important cellular factors without further growth or division of their own (Lim, J. W. and Bodnar, A., 2002). Examples of feeder layer cells are typically human diploid lung cells, mouse embryonic fibroblasts, Swiss mouse embryonic fibroblasts, but can be any post-mitotic cell that is capable of supplying cellular components and factors that are advantageous in allowing optimal growth, viability, and expansion of stem cells.

Cells in culture can be maintained either in suspension or attached to a solid support, such as extracellular matrix components and synthetic or biopolymers. Stem cells often require additional factors that encourage their attachment to a solid support, such as type I, type II, and type IV collagen, concanavalin A, chondroitin sulfate, fibronectin, "superfibronectin" and fibronectin-like polymers, gelatin, laminin, poly-D and poly-L-lysine, thrombospondin, and vitronectin.

B. Cryopreservation of Stem Cells/Tissue Containing Stem Cells

Human postnatal periodontal ligament multipotent stem cells can be collected and saved for future use through preservation techniques, such as freezing in liquid nitrogen. It is envisioned that such cells could be collected from the periodontal ligament of a subject, saved, and implanted into the same subject at a later time. Such a protocol would be useful for replacing cells lost due to age or trauma. For example, the saved cells could be used during periodontal reconstruction procedures later in life. In addition, cells can be treated with factors to induce them to form different phenotypes (e.g., differentiation).

Also disclosed herein is the first report of the isolation of functional stem cells from freeze-thawed solid tissue. As described herein, human cryopreserved PDLSCs (C-PDLSCs) isolated from frozen tissue maintained stem cell characteristics and in vivo tissue regeneration capacity, suggesting great potential for using C-PDLSCs for clinical purposes, including but not limited to periodontal tissue regeneration.

C. Methods for Genetically Altering PDLSCs

PDLSCs can be transfected with a preselected nucleic acid construct that would cause the cells to express a preselected product. These cells could then be implanted into the subject in order to administer the preselected product to the subject. Examples of preselected products include, but are not limited to, growth factors, hormones, cytokines, chemokines, factors related to hemophilia, and the like. Obtaining and implanting cells from the same subject is thought to avoid many complications resulting from immune rejection.

PDLSCs isolated by the methods described herein can be genetically modified by introducing DNA or RNA into the cell by a variety of methods known to those of skill in the art. These methods are generally grouped into four major categories: (1) viral transfer, including the use of DNA or RNA viral vectors (e.g., retroviruses (e.g., lentiviruses), Simian virus 40 (SV40), alphavirus vectors, including, but not limited to Sinbis virus, bovine papillomaviurs, adenovirus, adeno-associated virus, recombinant herpes viruses and the like); (2) chemical transfer, including calcium phosphate transfection and DEAE dextran transfection methods; (3) membrane fusion transfer using DNA-loaded membranous vesicles such as liposomes, red blood cell ghosts, and protoplasts, for example; and (4) physical transfer techniques, such as microinjection, electroporation, nucleofection, microprojectile gene transfer or direct "naked" DNA transfer.

Methods to prepare nucleic acid constructs are well known in the art and have been described (Sambrook et al., Molecular Cloning: A Laboratory Manual, 3rd edition, Cold Spring Harbor Press, Cold Spring Harbor, N.Y. (2001)).

Viral vectors for use in genetically-modifying PDLSCs include, but are not limited to, adenoviral (U.S. Pat. No. 5,824,544; U.S. Pat. No. 5,707,618; U.S. Pat. No. 5,693,509; U.S. Pat. No. 5,670,488; U.S. Pat. No. 5,585,362), retroviral (U.S. Pat. No. 5,888,502; U.S. Pat. No. 5,830,725; U.S. Pat. No. 5,770,414; U.S. Pat. No. 5,686,278; U.S. Pat. No. 4,861, 719), adeno-associated viral (U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479), adenoviral-adenoassociated viral hybrid (U.S. Pat. No. 5,856,152), a lentiviral vector, a vaccinia viral or a herpesviral (U.S. Pat. No. 5,879,934; U.S. Pat. No. 5,849,571; U.S. Pat. No. 5,830,727; U.S. Pat. No. 5,661,033; U.S. Pat. No. 5,328,688) vector.

Delivery of the expression constructs through non-viral vectors also is contemplated. Such delivery may employ microinjection (U.S. Pat. No. 5,612,205), electroporation (U.S. Pat. No. 5,507,724; U.S. Pat. No. 5,869,326; U.S. Pat. No. 5,824,547; U.S. Pat. No. 5,789,213; U.S. Pat. No. 5,749, 847; U.S. Pat. No. 5,019,034), calcium phosphate coprecipitation, DEAE dextran introduction, receptor mediated introduction, liposome mediated introduction (U.S. Pat. No. 5,631,018; U.S. Pat. No. 5,620,689; U.S. Pat. No. 5,861,314; U.S. Pat. No. 5,855,910; U.S. Pat. No. 5,851,818; U.S. Pat. No. 5,827,703, U.S. Pat. No. 5,785,987), dendrimer technology (U.S. Pat. No. 5,795,581; U.S. Pat. No. 5,714,166; U.S. Pat. No. 5,661,025), naked DNA injection, particle bombardment (U.S. Pat. No. 5,836,905; U.S. Pat. No. 5,120,657) and nucleofection (Lakshmipathy, U., et al., Stem Cells, 22:531-543 (2004)).

PDLSCs can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. Insertion of one or more pre-selected DNA sequences can be accomplished by homologous recombination or by viral integration into the host cell genome.

The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including, but not limited to the tamoxifen responsive mutated estrogen receptor) for expression in specific cell compartments (including, but not limited to, the cell membrane). Other elements that can enhance expression can also be included, such as an enhancer or a system that results in high levels of expression. Additionally, in some instances, it is desirable to have the gene product secreted. In such cases, the gene product preferably contains a secretory signal sequence that facilitates secretion of the protein.

Any of these techniques can also be applied to introduce a transcriptional regulatory sequence into PDLSC to activate a desired endogenous gene. This can be done by both homologous (e.g., U.S. Pat. No. 5,641,670) or non-homologous (e.g., U.S. Pat. No. 6,602,686) recombination.

Successful transfection or transduction of target cells can be demonstrated using genetic markers. The green fluorescent protein of Aequorea victoria, for example, has been shown to be an effective marker for identifying and tracking genetically modified cells (Persons, D. et al., Nature Medicine, 4:1201-1205 (1998)). Alternative selectable markers include the β-Gal gene, the truncated nerve growth factor receptor, and drug selectable markers (including, but not limited to, NEO, MTX, hygromycin).

In another embodiment, the PDLSCs can be derived from transgenic animals, and thus, are in a sense already genetically modified. There are several methods presently used for generating transgenic animals. The technique used most often is direct microinjection of DNA into single-celled fertilized eggs. Other techniques include retroviral-mediated transfer, or gene transfer in embryonic stem cells. Use of these transgenic animals has certain advantages including the fact that there is no need to transfect healthy cells. PDLSCs derived from transgenic animals will exhibit stable gene expression. Using transgenic animals, it is possible to breed in new genetic combinations. The transgenic animal may have integrated into its genome any useful gene.

When the genetic modification is for the production of a biologically active substance, the substance will generally be one that is useful for the treatment of a given injury and/or disease. For example, it may be desired to genetically modify cells so they secrete a certain growth factor, growth factor receptor or cytokine.

II. A Method to Produce Periodontal and Adipose Tissue within an Organism

The invention provides a method to produce periodontal and adipose tissue within a subject. The method for producing periodontal or adipose tissue involves transplanting a postnatal periodontal ligament multipotent stem cell(s) into the subject such that the desired product is formed. The postnatal periodontal ligament stem cell may be a human postnatal periodontal ligament multipotent stem cell.

A. Use of PDLSCs

The postnatal stem cells of the invention can be transplanted into an organism to prevent or reduce numerous maladies. For example, a postnatal stem cell of the invention may be transplanted into traumatized periodontium contained within a subject, such as a human, for the treatment of periodontal disease or other injury. In another example, a postnatal stem cell of the invention may be implanted into a subject to create fat when needed. Such fat creation can be used to reduce or ameliorate serious disorders (lypodystrophies) where fat is lacking in different or in all parts of the body.

These subjects often times experience severe problems related to energy metabolism, which is highly dependent upon fat.

The invention provides a method to generate periodontal tissue. The periodontal ligament stem cells may be obtained from a subject, such as a human, that is different than the subject into which the cells will be transplanted. Alternatively, periodontal ligament stem cells may be obtained from the same subject, such as a human, into which they will be transplanted. Immune rejection of transplanted cells may be avoided by obtaining cells from the same subject into which the cells will be transplanted.

The methods may be practiced in vitro under tissue culture conditions and/or under in vivo conditions. Briefly, periodontal ligament stem cells may be grown under tissue culture conditions, optionally genetically modified and then collected. The collected cells may then be placed in a periodontal region of interest within a subject such that the periodontal ligament stem cells produce periodontal tissue/cells, including periodontal ligament and cementum. The periodontal stem cells may be transplanted in combination with a carrier, or not in combination with a carrier.

Regenerative periodontal tissue production allows biological material to be replaced with newly formed biological material as opposed to artificial materials or traditional grafts. This may avoid an immune or allergic reaction to an artificial material that is implanted into a subject and cause less pain to the subject than currently available treatments. In addition, biological materials may be better maintained over time than artificial materials due to continuous cellular turnover.

Following administration, the immunological tolerance of the subject to the PDLSCs or progeny derived therefrom may be tested by various methods known in the art to assess the subject's immunological tolerance to PDLSCs. In cases where subject tolerance of PDLSCs is suboptimal (e.g., the subject's immune system is rejecting the exogenous PDLSCs), therapeutic adjunct immunosuppressive treatment, which is known in the art, of the subject may be performed.

B. Administration

For the purposes described herein, either autologous, allogeneic or xenogeneic PDLSCs can be administered to a subject, either in differentiated or undifferentiated form, genetically altered or unaltered, by direct injection to a tissue site, systemically, on or around the surface of an acceptable matrix, encapsulated or in combination with a pharmaceutically acceptable carrier. The postnatal stem cells may be expanded ex vivo prior to being implanted into an organism.

PDLSCs can be administered to a subject by a variety of methods known in the art. PDLSCs can be administered to a subject by localized or systemic injection, including but not limited to intramuscular injection and intravenous injection. PDLSCs may be administered within or in proximity to a site requiring new cells, mass, or enhanced function; alternatively they can be administered at a remote location.

In one embodiment, a cell suspension is drawn up into a syringe and administered to a subject. Multiple injections may be made using this procedure. The use of such cellular suspension procedures provides many advantages. For example, these methods direct cells to any predetermined site and are relatively non-traumatic.

Typically, the number of cells transplanted into a subject will be a "therapeutically effective amount." As used herein, a "therapeutically effective amount" refers to the number of transplanted cells that are required to effect treatment of the particular injury, or disease for which treatment is sought. For example, where the treatment is for tissue injury, transplantation of a therapeutically effective amount of cells will typically produce a reduction in the amount and/or severity of the symptoms associated with the injury. Persons of skill in the art will understand how to determine proper cell dosages.

A postnatal stem cell of the invention can be cultured under inducing conditions to cause the postnatal stem cell to differentiate into a desired cell type. This culturing may be conducted prior to transplantation of the differentiated, or partially differentiated cell, into a subject. For example, a postnatal stem cell of the invention may be subjected to adipocyte induction.

Alternatively, PDLSCs and their progeny can be induced to proliferate and/or differentiate in vivo by administering to the host, any growth factor(s), cytokine(s) or pharmaceutical composition(s) that will induce proliferation and differentiation of the cells. These growth factor(s), cytokine(s) or pharmaceutical composition(s) include any growth factor, cytokine or pharmaceutical composition known in the art, including the growth factors and cytokines described herein for in vitro proliferation and differentiation.

Cytokines include, but are not limited to, stromal cell derived factor-1 (SDF-1), stem cell factor (SCF), angiopoietin-1, placenta-derived growth factor (PlGF) and granulocyte-colony stimulating factor (G-CSF). Cytokines also include any which promote the expression of endothelial adhesion molecules, such as ICAMs, VCAMs.

Differentiation of PDLSCs to a desired phenotype can be enhanced when differentiation factors are employed.

The viability of newly forming tissues can be enhanced by angiogenesis. Differentiation factors promoting angiogenesis include, but are not limited to, VEGF, aFGF, angiogenin, angiotensin-1 and -2, betacellulin, bFGF, Factor X and Xa, HB-EGF, PDGF, angiomodulin, angiotropin, angiopoietin-1, prostaglandin E1 and E2, steroids, heparin, 1-butyryl-glycerol, and nicotinic amide.

Factors that decrease apoptosis can also promote the formation of new tissue. Factors that decrease apoptosis include, but are not limited to, β-blockers, angiotensin-converting enzyme inhibitors (ACE inhibitors), carvedilol, angiotensin II type 1 receptor antagonists, caspase inhibitors, cariporide, and eniporide.

Exogenous factors (e.g., cytokines, growth factors, differentiation factors and anti-apoptosis factors) can be administered prior to, after or concomitantly with PDLSCs. For example, a form of concomitant administration would comprise combining a factor of interest in the PDLSC suspension media prior to administration. Doses for administrations are variable, may include an initial administration followed by subsequent administrations; but nonetheless, can be ascertained by the skilled artisan, from this disclosure, the documents cited herein, and the knowledge in the art.

A method to potentially increase cell survival is to incorporate PDLSCs into a suitable matrix implant, including, but not limited to, a biopolymer or synthetic polymer or polymer matrix (so as to encapsulate the cells prior to introduction into the body of the subject, such as within a polymer capsule). Depending on the subject's condition, the site of injection might prove inhospitable for cell seeding and growth because of scarring or other impediments. Examples of biopolymer include, but are not limited to, cells mixed with biopolymers such as fibronectin, fibrin, fibrinogen, thrombin, collagen, and proteoglycans, which may be chemically modified or shaped. This could be constructed with or without cytokines, differentiation or additional genetic material. Additionally, these could be in suspension, but residence time at sites subjected to flow would be nominal.

Another alternative is a three-dimension gel with cells entrapped within the interstices of the cell/biopolymer admixture. Again differentiation factors or cytokines could be included within the gel. These could be delivered by injection by various routes.

The quantity of cells to be administered will vary for the subject being treated. In one embodiment, about $10^3$ to about $10^4$ to about $10^8$ or about $10^5$ to about $10^7$, or about $3\times10^7$ cells. However, the precise determination of what would be considered an effective dose may be based on factors individual to each subject, including their size, age, size of the infarct or other organ damage, and amount of time since the damage occurred. Therefore, dosages can be readily ascertained by those skilled in the art from this disclosure and the knowledge in the art.

The skilled artisan can readily determine the amount of cells and optional additives, vehicles, and/or carrier in compositions to be administered in methods of the invention. Typically, any additives (in addition to the active stem cell(s) and/or cytokine(s)) are present in an amount of 0.001 to 50 wt % solution, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

Of course, for any composition to be administered to an animal or human, and for any particular method of administration, it is preferred to determine therefore toxicity, such as by determining the lethal dose (LD) and $LD_{50}$ in a suitable animal model, e.g., rodent, such as mouse, and the dosage of the composition(s), concentration of components therein and timing of administering the composition(s), which elicit a suitable response. Such determinations do not require undue experimentation from the knowledge of the skilled artisan, this disclosure and the documents cited herein. Furthermore, the timing of sequential administrations can be ascertained without undue experimentation.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

Examples of compositions comprising PDLSCs include liquid preparations for administration, including suspensions; and, preparations for intramuscular or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The point is to use an amount, which will achieve the selected viscosity. Viscous compositions are normally prepared from solutions by the addition of such thickening agents.

A pharmaceutically acceptable preservative or cell stabilizer can be employed to increase the life of the compositions. Preferably, if preservatives are necessary, it is well within the purview of the skilled artisan to select compositions that will not affect the viability or efficacy of the PDLSCs as described in the present invention.

Those skilled in the art will recognize that the components of the compositions should be selected to be chemically inert. This will present no problem to those skilled in the chemical and pharmaceutical arts, or problems can be readily avoided by reference to standards texts or simple experiments.

Compositions can be administered in dosages and by techniques well known to those skilled in the medical and veterinary arts taking into consideration such factors as the age, sex, weight, and condition of the particular subject, and the composition form used for administration (e.g., solid vs. liquid).

Suitable regimes for initial administration and further doses for sequential administrations also are variable, may include an initial administration followed by subsequent administrations; but nonetheless, can be ascertained by the skill artisan, from this disclosure, the documents cited herein, and the knowledge in the art.

This invention is further illustrated by the following example, which is not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Isolation, Characterization and Use of PDLSCs

Materials and Methods

Samples and Cell Culture

Normal human impacted third molars (n=25) were collected from 16 individuals (19-29 years of age) at the Dental Clinic of the National Institute of Dental & Craniofacial Research, USA, following approved guidelines set by the National Institutes of Health Office of Human Subjects Research. Periodontal ligament (PDL) was gently separated from the surface of the root and then digested in a solution of 3 mg/ml collagenase type I (Worthington Biochem, Freehold, N.J.) and 4 mg/ml dispase (Roche, Mannheim, Germany) for 1 hour at 37° C. PDL samples from different individuals were pooled and single-cell suspensions were obtained by passing the cells through a 70 µm strainer (Falcon, BD Labware, Franklin Lakes, N.J., USA).

To identify putative stem cells, single-cell suspensions (1 to $1 \times 10^4$ cells) were seeded into 10-cm culture dishes (Costar, Cambridge, Mass.) with alpha-modification of Eagle's Medium (GIBCO BRL, Grand Island, N.Y., USA) supplemented with 15% fetal calf serum (Equitech-Bio Inc, Kerrville, Tex., USA), 100 µmol/L ascorbic acid 2-phosphate (WAKO, Tokyo, Japan), 2 mmol/L glutamine, 100 U/ml penicillin and 100 µg/ml streptomycin (Biofluids Inc, Rockville, Md., USA), then incubated at 37° C. in 5% $CO_2$.

To assess colony-forming efficiency, day 10 cultures were fixed with 4% formalin, and then stained with 0.1% toluidine blue. Aggregates of 50 or more cells were scored as colonies. The proliferation rate of sub-confluent cultures (first passage) of stem cells was assessed by bromodeoxyuridine (BrdU) incorporation for 24 hours, with a Zymed Laboratories BrdU staining Kit (Vector Laboratories, Burlingame, Calif., USA). Calcium accumulation was induced as described in Miura at al. (2003), and was detected by staining with 2% alizarin red S (pH 4.2) staining. Calcium concentration was measured with a Sigma calcium kit 587-A (Sigma Diagnostics, St. Louis, Mo., USA). The induction of adipogenesis was carried out as reported in Gronthos et al. (2000).

Dental pulp stem cells (DPSCs) and bone marrow stromal stem cells (BMSSCs) were isolated and cultured as previously described (Gronthos et al. 2000; Krebsbach et al., 1997; Shi et al., 2003). In some experiments, PDL stem cells (PDLSCs) and DPSCs were obtained from the same donor or donors. BMSSCs were obtained from a commercially available resource (AllCells LLC, Berkeley, Calif., USA). All primary cells used in this study were at 2-4 passages. For each experiment, the same passage of PDLSCs, DPSCs and BMSSCs was used.

Antibodies

Rabbit antibodies used included anti-HSP90 and TGFβR1 (Santa Cruz Biotechnology, Inc., Santa Cruz, Calif., USA); anti-CBFA1 (Oncogene Research Product, Cambridge, Mass., USA); anti-endostatin and anti-human-specific mitochondria (Chemicon, Temecula, Calif., USA); anti-alkaline phophatase (LF-47), anti-osteocalcin (LF-32), anti-matrix extracellular protein (MEPE; LF-155), anti-type I collagen (LF-67), anti-fibromodulin (LF-150) from Dr. Larry Fisher of National Institute of Dental and Craniofacial Research, National Institutes of Health (Miura et al., 2003). Mouse antibodies used included anti-CD146/MUC18, and anti-STRO-1 (Dr. Stan Gronthos; Shi et al., 2003); anti-bone sailoprotein (LF-25, from Dr. Larry Fisher). Rabbit and murine isotype-matched negative control antibodies were also used from Caltag Laboratories (Burlingame, Calif., USA).

RT-PCR

The PCR primers included: PPARγ2—sense, 5'-CTC-CTATTGACCCAGAAAGC-3' (SEQ ID NO: 1; 114-133), antisense, 5'-GTAGAGCTGAGTCTTCTCAG-3' (SEQ ID NO: 2; 441-460, Genbank accession number: XM_003059); LPL—sense, 5'-ATGGAGAGCAAAGCCCTGCTC-3' (SEQ ID NO: 3; 175-195), antisense, 5'-GTTAGGTC-CAGCTGGATCGAG-3' (SEQ ID NO: 4; 718-738, Genbank accession number: XM_044682); GAPDH—sense, 5'-AGCCGCATCTTCTTTTGCGTC-3' (SEQ ID NO: 5; 12-32), antisense, 5'-TCATATTTGGCAGGTTTTTCT-3' (SEQ ID NO: 6; 807-827, Genbank accession number: M33197). Total RNA isolation, first-strand cDNA synthesis and PCR processes were as previously described (Gronthos et al., 2002).

Northern Blot Analysis

15 µg total RNA from primary PDLSC, DPSC and BMSSC cultures was electrophoresed and then transferred to a nylon membrane. Probe was generated from purified PCR products with scleraxis (SCX) primers (sense, 5'-CTGGCCTCCAGC-TACATCTC-3', 900-919 (SEQ ID NO:7), antisense, 5'-CTTTCTCTGGTTGCTGAGGC-3', 1090-1109 (SEQ ID NO:8), Genbank accession number: Bk000280) by random labeling with (γ-$^{32}$P) dCTP (Dupont New England Nucleotide) using the Stratagene Prime It II labeling kit (Stratagene). After prehybridization in QuickHyb hybridization solution (Stratagene, Cedar Creek, Tex.) at 68° C. for 15 minutes, the membranes were hybridized with SCX probe at 68° C. for 1 hour. The membranes were washed twice in 2×SSC, 0.1% (w/v) SDS for 15 minutes at room temperature, followed by one wash in 0.1% SSC and 0.1% (w/v) SDS at 68° C. for 30 minutes. The membranes were exposed to a PhosphoImager cassette (Amersham Bioscience, Sunnyvale, Calif., USA) for 16-72 hours.

Immunohistochemistry

PDLSCs were subcultured into 8-chamber slides ($2 \times 10^4$ cells/well) (NUNC Inc, Naperville, Ill., USA). The cells were fixed in 4% formaldehyde for 15 minutes and then blocked and incubated with primary antibodies (at dilutions ranging from about 1:200 to about 1:500) for 1 hour. The samples were subsequently incubated with goat secondary antibodies of either IgG-rhodamine red or IgG-Cy2 (Jackson ImmunoResearch, West Grove, Pa., USA), for 45 minutes. Isotype-matched control antibodies were used under the same conditions. For enzymatic immunohistochemical staining, the Zymed broad spectrum immunoperoxidase AEC kit (Zymed Laboratories Inc., South San Francisco, Calif., USA) was used according to the manufacturer's protocol.

Western Blot Analysis

Primary antibodies used for western blot were the same as those used in immunohistochemical staining at dilutions ranging from about 1:200 to about 1:1000. Western blot analysis was carried out as reported in Shi et al., 2001.

Immunomagnetic Isolation

This procedure was reported previously in Shi and Gronthos, 2003. Briefly, single-cell suspensions of PDLSCs were incubated with STRO-1 supernatant (murine anti-human BMSSCs, IgM) for 1 hour on ice. The cells were then washed with PBS/1% bovine serum albumin, and resuspended with rat anti-mouse IgM-conjugated Dynal beads at four beds per cell (Dynal, Oslo, Norway) for 45 on a rotary mixer at 4° C. bead-positive cells were isolated with a Dynal MPC-1 magnetic particle concentrator according to the manufacturer's recommendations.

Transplantation

Approximately $4.0 \times 10^6$ of in vitro expanded PDLSCs were transplanted subcutaneously into the dorsal surface of twelve 10-week-old immunocompromised beige mice (NIH-bg-nu-xid, Harlan Sprague Dawley, Indianapolis, Ind., USA) as described in Gronthos et al. 2000 and Krebsbach et al., 1997. The same number of in vitro expanded DPSCs and BMSSCs were used as controls. These procedures were performed in accordance with specifications of an approved animal protocol (NIDCR #02-222).

PDLSCs were transplanted into the periodontal area in six immunodeficient rats as described previously (Melcher 1970). Briefly, $2.0 \times 10^6$ PDLSCs were mixed with 40 mg of hydroxyapatite/tricalcium phosphate ceramic particles (Zimmer, Warsaw, Ind., USA) and transplanted into two 2 $mm^2$ periodontal defects that had been surgically created on the buccal cortex of the mandibular molar in the rats (NIH-mu, Taconic, Germantown, N.Y., USA). These procedures were performed in accordance with specifications of an approved small-animal protocol (NIDCR #03-264). The transplants were recovered at 6-8 weeks post-transplantation, fixed with 4% formalin, decalcified with buffered 10% ethylenediaminotetraacetic acid (EDTA) (pH 8.0), and then embedded in paraffin. Sections were deparaffinized and stained with hematoxylin and eosin.

Statistical Analysis

Wilcoxon rank-sum test was used to analyze the significance between the two groups. p values less than 0.05 was considered to be statistically significant.

Results

To identify putative stem cells, single-cell suspensions were generated from human PDL (FIGS. 1A and 1B). The ability of PDL-derived cells to form adherent clonogenic cell clusters of fibroblast-like cells, similar to those recorded for different mesenchymal stem-cell populations, was shown by the formation of about 170 single colonies (FIG. 1C), generated from $10^5$ single cells cultured at low density (FIG. 1I). This colony-forming cell population, which is referred to herein as periodontal ligament stem cells (PDLSCs), has a high uptake rate of bromodeoxyuridine, similar to the rate seen with DPSCs (FIG. 1D).

Ex-vivo expanded PDLSCs expressed the cell surface molecules STRO-1 and CD146/MUC18, two early mesenchymal stem-cell markers also present on BMSSCs and DPSCs (FIGS. 1E and 1F). STRO-1-positive cells were also shown to be located in the PDL tissue by immunohistochemical staining (FIGS. 1G and 1H). When anti-STRO-1 antibody was used to isolate PDLSCs released from freshly collected PDL tissue, most colony-forming cells were found to be contained within the STRO-1-positive cell population, confirming STRO-1 as an early progenitor marker for PDLSCs (FIG. 1I).

The expression level of scleraxis, a tendon-specific transcription factor, was assessed in PDLSCs, since PDL is similar to tendon with respect to its dense collagen fiber structure and its ability to absorb mechanical stress during normal physiological activity. PDLSCs expressed a higher level of scleraxis than did BMSSCs and DPSCs (FIG. 1J), suggesting that PDLSCs might belong to a unique population of postnatal mesenchymal stem cells.

Figure 2:
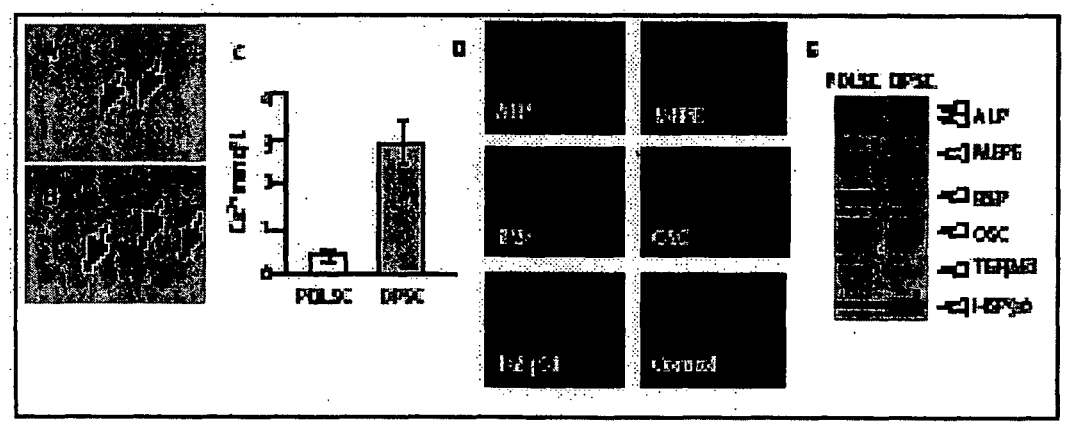
FIG. 2 expression of cementoblastic/osteoblastic phenotype by PDLSCs. Alizarin red staining showed limited amounts of mineralized nodule formation in PDLSC cultures (A). Compared with induced DPSC cultures (B), PDLSC cultures accumulated smaller amounts of calcium than did DPSCs (p=0.0026, C). (D) Immunocytochemical staining showed that PDLSCs expressed cementoblastic/osteoblastic markers, including alkaline phosphatase (ALP), matrix extracellular protein (MEPE), bone sialoprotein (BSP), osteocalcin (OSC), and TGFβ receptor type I (TGFβR1). (E) Western blot analysis confirmed the expression of the cementoblastic/osteoblastic markers; HSP90 was used to assess the amount of protein loaded per sample.

To investigate the potential of PDLSCs to undergo cementoblastic/osteoblastic differentiation, established secondary PDLSC cultures were supplemented with L-ascorbate-2-phosphate, dexamethasone, and inorganic phosphate to induce mineralization in vitro as previously described (Gronthos et al., 2000). Small round alizarin red-positive nodules formed in the PDLSC cultures after 4 weeks of induction, indicating calcium accumulation in vitro (FIG. 2A). However, compared with DPSCs, PDLSCs formed fewer mineralized nodules, which correlated with lower concentrations of calcium in the extracellular matrix (FIG. 2A-2C). Immunohistochemical staining (FIG. 2D) and western blot analysis (FIG. 2E) showed that cultured PDLSCs expressed an array of cementoblastic/osteoblastic markers, including alkaline phosphatase, MEPE, bone sialoprotein, osteocalcin, and TGFβ receptor type I. After PDLSCs differentiated into cementoblasts and cementocytes, they continued to express bone/cementum markers such as BSP, MEPE, OSC, and type I collagen. The newly formed cementum expressed a specific marker, fibromodulin, that was not expressed in bone generated by other cells.

Figure 3:
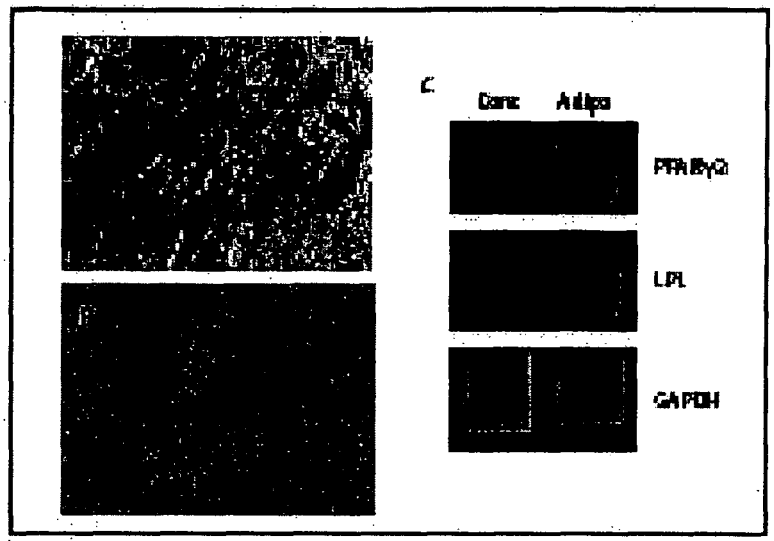
FIG. 3 demonstrates adipogenic differentiation of PDLSCs. (A) Cultured PDLSCs formed oil red 0 positive lipid clusters after 3 weeks of induction in the presence of 0.5 mM isobutylmethylxanthine, 0.5 µM hydrocortisone, and 60 µM indomethacin. (B) Standard culture medium did not induce any oil red O positive lipid clusters. (C) Substantial upregulation of adipogenic markers PPARγ2 and lipoprotein lipase (LPL), was observed in the group induced with the adipogenic cocktail (Adipo) compared with the control group (Cont) by RT-PCR.

Whether PDLSCs, like DPSCs, had the potential to differentiate into other cell lineages, such as adipocytes, was investigated. After 3 weeks of culture with an adipogenic inductive cocktail, PDLSCs developed into oil red O-positive lipid-laden fat cells (FIGS. 3A and 3B). This development correlated with an upregulation in the expression of two adipocyte specific transcripts, PPARγ2 and lipoprotein lipase, as detected by RT-PCR (FIG. 3C).

Figure 4:
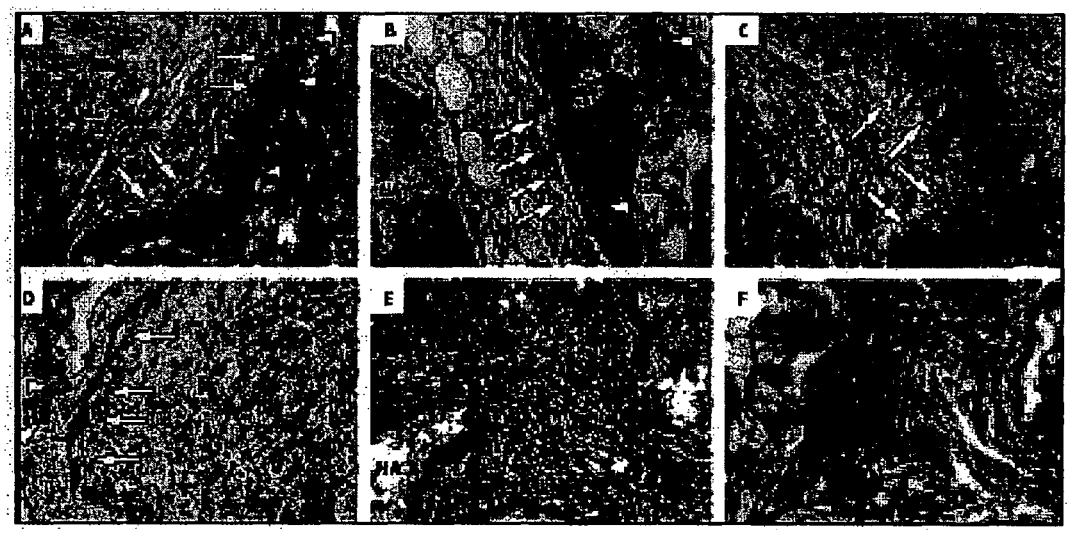
FIG. 4 demonstrates the generation of cementum-like and PDL-like structures in vivo by PDLSCs. (A) After 8 weeks of transplantation, PDLSCs differentiated into cementoblast-like cells (arrows) that formed a cementum-like structure (C) on the surface of the hydroxyapatite tricalcium phosphate (HA) carrier; cementocyte-like cells (triangles) and PDL-like tissue (PDL) were also generated. (B) BMSSC transplant was used as control to show the formation of a bone/marrow structure containing osteoblasts (arrows), osteocytes (triangles), and elements of bone (B) and haemopoietic marrow (HP). (C) DPSC transplant was also used as a control to show a dentin/pulp-like structure containing odontoblasts (arrows) and dentin-like (D) and pulp-like (Pulp) tissue. (D) Immunohistochemical staining showed that PDLSCs generated cementum-like structure (C) and differentiated into cementoblast-like cells (arrows) and cementocyte-like cells (triangles) that stained positive for human-specific mitochondria antibody. Part of the PDL-like tissue (PDL) also stained positive for human specific mitochondria antibody (within dashed line). (E) Of 13 selected strains of single-colony derived PDLSC, eight (61%) generated cementum/PDL-like structures in vivo as shown at lower magnification (approximately ×20). New cementum-like structure (C) formed adjacent to the surfaces of the carrier (HA) and associated with PDL-like tissue (PDL). (F) The other five strains did not generate mineralized or PDL-like tissues in vivo.
Figure 5:
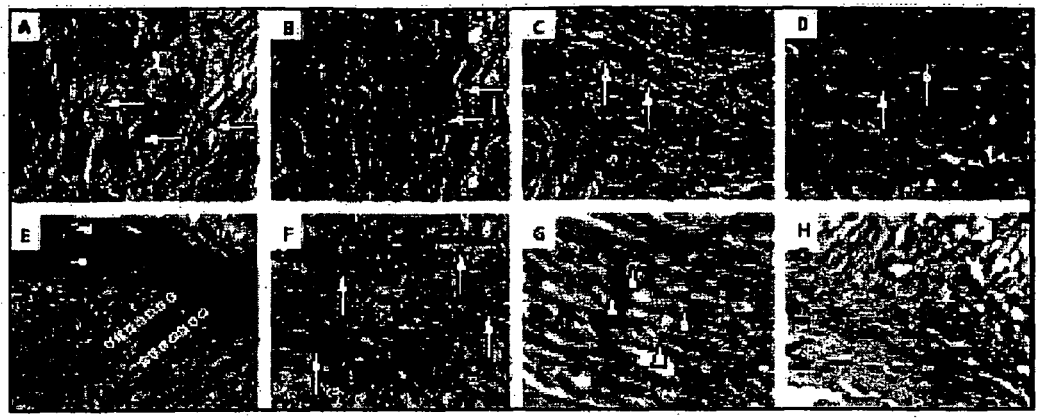
FIG. 5 depicts the generation of collagen fibers by PDLSCs in vivo. (A) Haematoxylin and eosin staining of human PDL tissue showing collagen fibers (arrows). (B) Collagen fibers of human PDL were positive for anti-type I collagen antibody staining (arrows). (C) Transplanted PDLSCs generated collagen fibers (arrows) along with the newly formed cementum-like structure (C). (D) These fibers were positive for anti-type I collagen antibody staining (arrows), similar to human PDL. (E) Transplanted PDLSCs formed cementum-like structures (C) that connected to newly formed collagen fibers (yellow dashed lines), similar to the structure of Sharpey's fiber. (F) Transplanted PDLSCs generated a substantial amount of collagen fibers (arrows). (G) These collagen fibers were positive for anti-human specific mitochondria antibody staining (triangles). (H) Pre-immunoserum was used as a negative control of PDLSC transplant for anti-human specific mitochondria antibody.

To validate the capacity of PDLSCs to differentiate into functional cementoblast-like cells, ex-vivo-expanded PDLSCs were transplanted into immunocompromised mice. A typical cementum/PDL-like structure was regenerated, in which a thin layer of cementum-like tissue formed on the surface of the carrier, along with condensed collagen fibers with sparse cells that resembled PDL structures (FIG. 4A). The cementum/PDL-like structures appeared totally different from typical bone/marrow structures generated by BMSSCs and dentin/pulp-like structures generated by DPSCs (FIGS. 4B and 4C). These findings showed the difference in capacity for tissue regeneration between PDLSC and BMSSC/DPSC in vivo. The PDLSC transplants contained human-specific mitochondria-positive cementum-forming cells and a PDL-like structure containing human PDLSCs as well as recipient cells (FIG. 4D). Of 13 single-colony-derived PDLSC clones transplanted into immunocompromised mice, eight (61%) showed a capacity to form a cementum/PDL-like tissue, equivalent to multicolony-derived PDLSCs (FIG. 4E). The remaining five clones did not form cementum/PDL-like tissues (FIG. 4F).

Transplanted human PDLSCs were able to form a dense type I collagen-positive PDL-like tissue within the transplants (FIG. 5A to 5D). More importantly, collagen fibers generated in vivo were able to connect with newly formed cementum-like structures that mimicked physiological attachment of Sharpey's fiber (FIG. 5E), which is needed to form functional attachment of cementum/PDL structures. These results suggest that PDLSCs may contain a subpopulation of cells capable of differentiating into cementoblasts/cementocytes and collagen-forming cells in vivo. Human PDLSCs were responsible for collagen fiber formation within the transplants, as shown by the reactivity of these cells with human-specific anti-mitochondria antibody (FIG. 5F to 5H).

Figure 6:
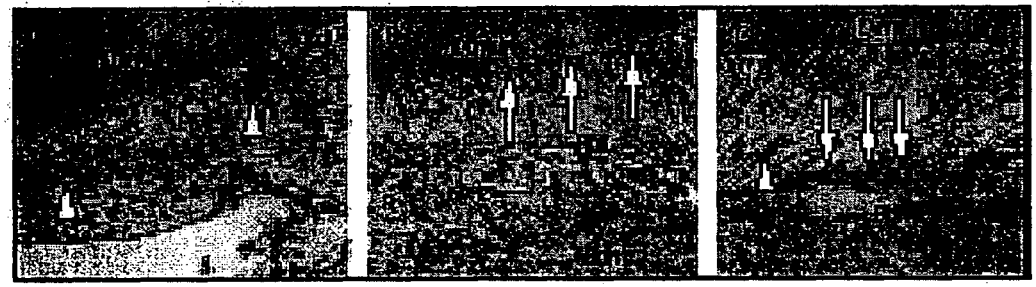
FIG. 6 depicts PDLSCs in periodontal tissue repair in immunocompromised rats. Immunohistochemical staining of recovered transplant tissue with human-specific anti-mitochondria antibody showed that human PDLSCs: (A) were located in the PDL compartment (triangles), (B) were involved in the attachment of PDL to the tooth surface (arrows), and (C) participated in repair of alveolar bone (arrows) and PDL (triangle).

To assess whether PDLSCs were able to contribute to periodontal tissue repair, human PDLSCs were transplanted into surgically created defects at the periodontal area of mandibular molars in immunocompromised rats. Transplanted human PDLSCs integrated into the PDL compartment in two of six examined samples (FIG. 6A), and occasionally attached to surfaces of alveolar bone and teeth (FIGS. 6B and 6C), dependent on the areas examined. These findings suggest a potential functional role of human PDLSCs for periodontal tissue regeneration.

Discussion

From the aspect of tooth development, PDL is derived from the dental follicle that surrounds developing teeth, providing a pool of cementum-forming cells (Handa et al. 2002; Zhao et al., 2002). The findings presented herein demonstrate that human PDL contains a population of multipotent postnatal stem cells that can be isolated and expanded in vitro, providing a unique reservoir of stem cells from an accessible tissue resource. Importantly, PDL collected from one tooth can give rise to many stem cells, because of their capacity for proliferation ex vivo. Therefore, tissue regeneration mediated by human PDLSCs might have potential as a practical cellular-based treatment for periodontal diseases.

Previous experiments have shown that human bone marrow and dental pulp tissue contain postnatal stem cells that are capable of differentiating into osteoblasts/odontoblasts, adipocytes, and neuronal-like cells. These stem cells were characterized as STRO-1/CD146-positive progenitors derived from a perivascular niche within the bone marrow and dental pulp microenvironments. (Gronthos et al., 2000; Shi et al., 2003; Gronthos et al., 2002) In the present study, it was demonstrated that the PDLSCs are similar to other mesenchymal stem cells with respect to their expression of STRO-1/CD146, suggesting that PDLSCs might also be derived from a population of perivascular cells. (Gould et al., 1977; McCulloch et al., 1985)

The findings presented herein suggest that PDLSCs represent a novel population of multipotent stem cells, as shown by their capacity to develop into cementoblast-like cells, adipocytes in vitro, and cementum/PDL-like tissue in vivo, and by their high expression of scleraxis, a specific transcription factor associated with tendon cells. (Brent et al., 2003) PDLSCs also showed the capacity to form collagen fibers, similar to Sharpey's fibers, connecting to the cementum-like tissue, suggesting the potential to regenerate PDL attachment. These data lend further support to the notion that PDLSCs are a unique population of postnatal stem cells. However, because of the heterogeneity of STRO-1/CD146-positive mesenchymal stem cells, (Shi et al., 2003) it is possible that PDLSCs described herein may represent a heterogeneous stem-cell-enriched population that contains some early uncommitted progenitor cells.

The osteogenic potential of PDL cells has been assessed previously with several cell-culture methods, and the ability of such cultures to form a mineralized matrix has been noted. (Lekic et al., 2001; Ohno et al., 2002). The data presented herein demonstrate the potential of PDLSCs to form calcified deposits in vitro, as previously shown with other mesenchymal stem-cell populations such as BMSSCs and DPSCs. However, PDLSCs formed sparse calcified nodules compared with their bone marrow and pulp tissue counterparts. Although PDLSCs were found to express an array of cementoblastic/osteoblastic markers, they did not form dentin or bone and its associated haemopoietic components in vivo.

This data presented herein used colony selection and STRO-1/CD146 markers to isolate PDLSCs from PDL. In-vivo transplantation showed that in vitro-expanded PDLSCs generate a cementum/PDL-like complex characterized by a layer of aligned cementum-like tissues and clearly associated PDL-like tissues. PDLSCs, like DPSCs, show a higher number of population doublings than do BMSSCs in culture; the potential mechanisms contributing to the long lifespan of PDLSCs and DPSCs are not clear. Even though PDLSCs, DPSCs, and BMSSCs are mesenchymal stem cells, and share some common protein expression profiles, PDLSCs differ significantly in their developmental potentials in vivo and their ability to develop into distinct tissues representative of the microenvironments from which they were derived in vivo.

The finding presented herein show that postnatal PDLSCs are clonogenic, highly proliferative cells and capable of regenerating cementum/PDL-like tissues, properties that effectively define them as stem cells. Consequently, PDLSCs have potential for use in periodontal tissue regeneration. The results presented herein show that human PDLSCs participate in the process of periodontal tissue repair in immunocompromised rats.

Example 2

Recovery of Functional Postnatal Stem Cells from Cryopreserved Human Mesenchymal Tissues, Such as Periodontal Ligament Introduction Postnatal stem cells have been successfully isolated from a variety of human tissues including bone marrow, peripheral blood, neural tissue, skeletal muscle, epithelium, dental pulp, and periodontal ligament (Bianco and Robey, 2001; Evers et al., 2003; Gronthos et al., 2000; Korbling and Estrov, 2003; Seo et al., 2004). With recent advances in stem cell therapies and tissue engineering, the effective preservation of stem cells is an issue for stem cell-mediated clinical treatment (Korbling and Estrov, 2003). Cryopreserved hematopoietic stem cells have been utilized for disease treatment in clinics for decades. Recently, it has been reported that hematopoietic stem cells can be successfully used for stem cell transplantation following 15 years of cryopreservation (Broxmeyer et al., 2003), suggesting long-term cryopreservation is a reliable approach for stem cell storage. Additionally, the ability to successfully cryopreserve reproductive cells including spermatozoa and oocytes, reproductive tissues, embryos, and nuclear material has significant implications for reproductive technology and medicine (He et al., 2003; Hoffman et al., 2003; Hubel, 1997; Rowley et al., 2003; Woods et al., 2004). However, whether cryopreserved solid human tissue is a resource for retrieving functional stem cells is unknown.

As described herein, human periodontal ligament stem cells (PDLSCs) were isolated and characterized as a population of multipotent stem cells capable of forming cementum and periodontal ligament tissues upon in vivo transplantation. Periodontal ligament tissue collected from extracted teeth is an easily accessible human tissue that may not only serve as a practical resource for potential stem-cell-mediated therapies but may also provide a sufficient number of tissue samples for the analysis of stem cell characteristics.

Materials and Methods

Subjects Cryopreservation and Cell Culture

Normal human impacted third molars and attached bone chips were collected immediately following extraction from a total of 10 adults (19-29 years of age) at the Dental Clinic of the National Institute of Dental & Craniofacial Research under approved guidelines set by the National Institutes of Health Office of Human Subjects Research. Periodontal ligaments were gently separated from the surface of the root, and then they were minced into small pieces (0.5 mm$^3$ in size). Bone marrow stromal tissues were mechanically removed from the bone chips (Krebsbach et al., 1997; Kuznetsov et al., 1997).

The PDL tissues or bone marrow stromal tissues derived from the different individuals were mixed together, and half of the tissue sample was utilized for isolating fresh stem cells while the remaining half was mixed with fetal calf serum (Equitech-Bio Inc, Kerrville, Tex.) containing 10% dimethyl sulfoxide (DMSO) at 4° C. and then directly stored into liquid nitrogen. After being frozen for 3 and 6 months, the tissues were thawed rapidly at 37° C. and subsequently digested in a solution of 3 mg/ml collagenase type I (Worthington Biochem, Freehold, N.J., USA) and 4 mg/ml dispase (Roche, Mannheim, Germany) for one hour at 37° C. Single cell suspensions ($10^4$ cells) were seeded into T25 flask (Costar, Cambridge, Mass.) with alpha Modification of Eagle's Medium (GIBCO BRL, Grand Island, N.Y., USA), supplemented with 15% fetal calf serum (Equitech-Bio Inc, Kerrville, Tex., USA), 100 mM L-ascorbic acid 2-phosphate (WAKO, Tokyo, Japan), 2 mM L-glutamine, 100 U/ml penicillin and 100 mg/ml streptomycin (Biofluids Inc, Rockville, Md., USA), and then incubated at 37° C. in 5% $CO_2$.

To assess colony-forming efficiency, day 10 cultures were fixed with 4% formalin, and then stained with 0.1% Toluidine blue. Aggregates of ≥50 cells were scored as colonies. The proliferation rate of sub-confluent cultures (first passage) of PDLSCs was assessed by bromodeoxyuridine (BrdU) incorporation for 12 hours, using a Zymed Laboratories BrdU staining Kit (Vector Laboratories, Burlingame, Calif., USA). Conditions for the induction of calcium accumulation and adipogenesis were as previously reported (Gronthos et al., 2000; Gronthos et al., 2002). For in vitro type I collagen generation, the PDLSC pellet ($2 \times 10^6$) was cultured for 6 weeks in 15 ml polypropylene tubes in 1 ml of high glucose (4.5 g/L) DMEM medium supplemented with 1% ITS+, 100 mM L-ascorbic acid 2-phosphate (WAKO, Tokyo, Japan), 2 mM L-glutamine, 100 U/ml penicillin and 100 mg/ml streptomycin (Biofluids Inc, Rockville, Md., USA), 2 mM pyruvate and freshly added 10 ng/ml TGF-β1. The medium was changed twice a week.

Antibodies

Rabbit antibodies included anti-TGFβRI (Santa Cruz Biotechnology, Inc., Santa Cruz, Calif., USA), anti-human-specific mitochondria (Chemicon, Temecula, Calif., USA), and anti-type I collagen (LF-67), bone sialoprotein (BSP LF-120), alkaline phosphate (ALP LF-47) from Dr. Larry Fisher of NIDCR/NIH (Miura et al., 2003). Mouse antibodies included STRO-1 (Dr. Stan Gronthos). Rabbit and murine isotype-matched negative control antibodies were also used (Caltag Laboratories, Burlingame, Calif., USA).

Transplantation

Approximately $2.0 \times 10^6$ of in vitro expanded C-PDLSCs or BMSSCs were mixed with 40 mg of hydroxyapatite/tricalcium phosphate (HA/TCP) ceramic particle (Zimmer Inc, Warsaw, Ind., USA) and then transplanted subcutaneously into the dorsal surface of 10-week-old immunocompromised beige mice (NIH-bg-nu-xid, Harlan Sprague Dawley, Indianapolis, Ind., USA) as previously described (Krebsbach et al., 1997; and herein). These procedures were performed in accordance with specifications of an approved animal protocol (NIDCR #02-222). The transplants were recovered at 6-8 weeks post-transplantation, fixed with 4% paraformaldehyde, decalcified with buffered 10% EDTA (pH 8.0), and then embedded in paraffin. Sections were deparaffinized and stained with H&E.

Immunohistochemistry C-PDLSCs were sub-cultured into 8-chamber slides ($2 \times 10^4$ cells/well) (NUNC Inc, Naperville, Ill.). The cells were fixed in 4% paraformaldehyde for 15 minutes and then blocked and incubated with primary antibodies (dilutions ranging from about 1:200 to about 1:500 dilution) for 1 hour. The samples were subsequently incubated with goat secondary antibodies of either IgG-Rhodamine Red or IgG-Cy2 (Jackson ImmunoResearch, West Grove, Pa., USA), for 45 minutes. For enzymatic immunohistochemical staining, the Zymed broad spectrum immunoperoxidase AEC kit (Zymed Laboratories Inc. South San Francisco, Calif., USA) was used according to the manufacturer's protocol.

Human Alu In Situ Hybridization

A human-specific Alu in situ hybridization was done as previously described (Shi et al., 2002). Briefly, primers for Alu (GenBank Accession Number X53550) included: sense, 5'-TGGCTCACGCCTGTAATCC-3' (base number 90-108; SEQ ID NO:9), and antisense: 5'-TTTTTTGAGACG-GAGTCTCGC-3' (base number 344-364; SEQ ID NO:10). Sections of eight week BMSSC transplants were deparaffinized and hybridized with the digoxigenin-labeled alu probe using the mRNA locator-Hyb Kit (Cat #1800; Ambion, Inc., Austin Tex.). After hybridization, the presence of human specific Alu positive cells was detected by immunoreactivity with antidigoxigenin alkaline phosphatase conjugated Fab fragments (Boehringer Mannheim, Indianapolis, Ind., USA).

Statistical Analysis

Student t-test was used to analyze the significance between the two groups. P values less than 0.05 were considered as statistically significant.

Results

Figure 7:
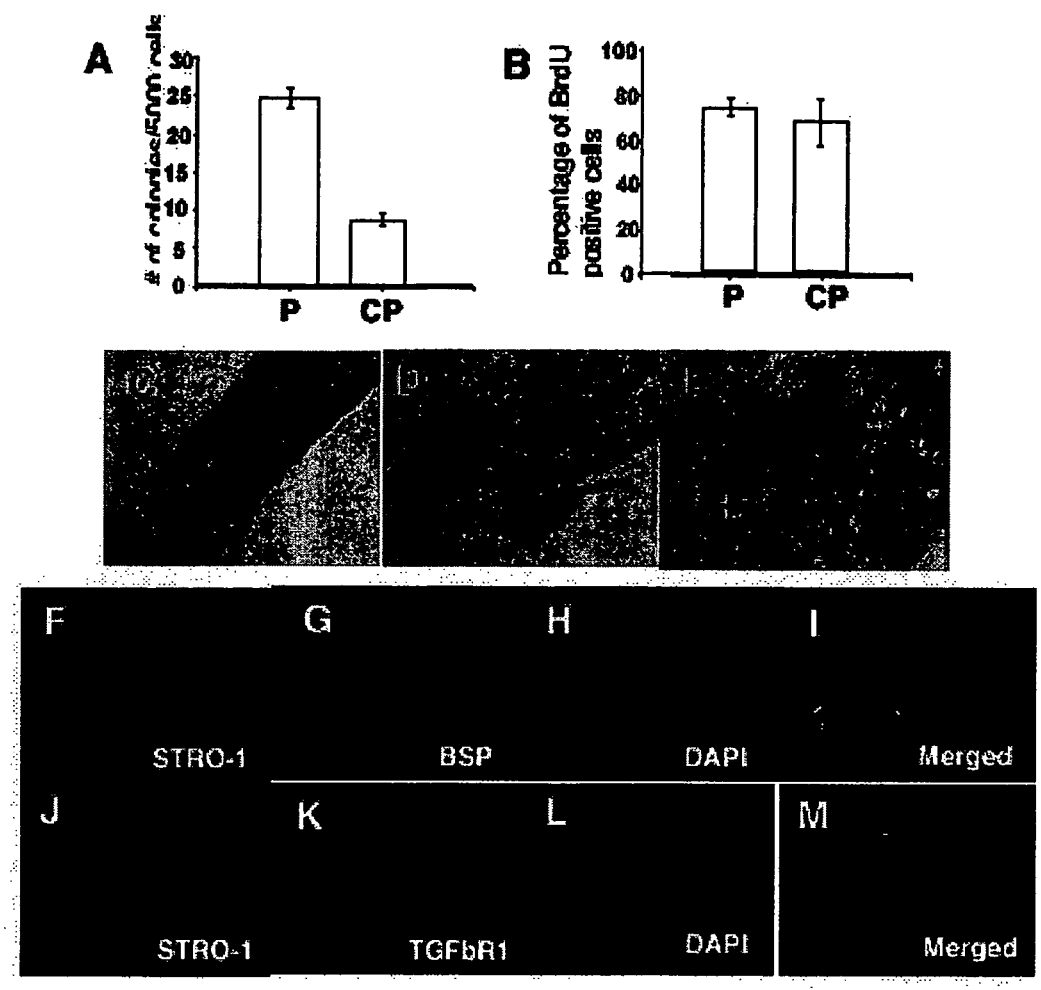
FIG. 7 demonstrates the isolation of C-PDLSCs. (A) PDLSCs recovered from 6 month cryopreserved PDL were capable of forming heterogenous single colony clusters after being plated at low density and cultured with regular culture medium for ten days as described in the methods. The number of single colonies derived from cryopreserved PDL (CP) was significantly decreased (*p<0.05) in comparison with the fresh non-frozen PDL (P) when the same number (5000) of cells were plated. (B) The proliferation rates were assessed by bromodeoxyuridine (BrdU) incorporation for 12 hours. C-PDLSCs (CP) maintain a high level of proliferation rate, similar to the regular PDLSCs (P), showing that there is no significant difference between the regular PDLSCs and C-PDLSCs. (C) H& E staining of non-frozen human PDL tissue. (D and E) H&E staining of PDL cryopreserved for 6 months. Most areas of PDL tissue showed a normal histological structure. However, some nuclear anisokaryosis was found in frozen PDL (E, arrow), indicating that the cryopreservation can cause some tissue damage. (F-M) C-PDLSCs expressed STRO-1, one of the early progenitor markers for mesenchymal stem cells. The C-PDLSCs may co-express STRO-1 with bone sialoprotein (BSP) and TGFβ receptor type I (TGFβR1) as shown on the merged figures. Some C-PDLSCs may express STRO-1 and BSP separately.

To examine whether cryopreserved tissue contained postnatal stem cells, small pieces of PDL were preserved frozen in the liquid nitrogen for 3 and 6 months and then the frozen PDL was used as a tissue resource to isolate postnatal stem cells. At least 40% of heterogeneous single colony strains of PDLSCs could be recovered from frozen-thawed PDL when they were plated at a low density (5000 cells per T-25 flask) (FIG. 7A). Although the number of PDLSC single colonies derived from cryopreserved PDL was significantly decreased in comparison with the fresh isolated PDLSCs, they maintained a high proliferative capacity in terms of BrdU labeling for 12 hours (FIG. 7B). Following histological examination of cryopreserved PDL, the frozen PDL tissue exhibited various normal types of microscopic structure in the majority of the areas examined (FIGS. 7C and 7D). However, cellular damage, such as anisokaryosis, variable size of nucleus, and clumping of cells, was noted (FIG. 7E). These cells were also negative for TUNEL staining, indicating non-apoptotic cell death probably caused by the nucleation of lethal intracellular ice.

Ex vivo expanded cryopreserved PDLSCs (C-PDLSCs) were found to express the cell surface molecule STRO-1, an early mesenchymal stem cell marker, along with the co-expression of cementoblastic/osteoblastic markers TGFβR1 and BSP (FIG. 7F-M). In addition, C-PDLSCs exhibited a separated and non-overlapped expression of STRO-1 with BSP (FIG. 2F-I), indicating their characteristics of heterogeneity.

Figure 8:
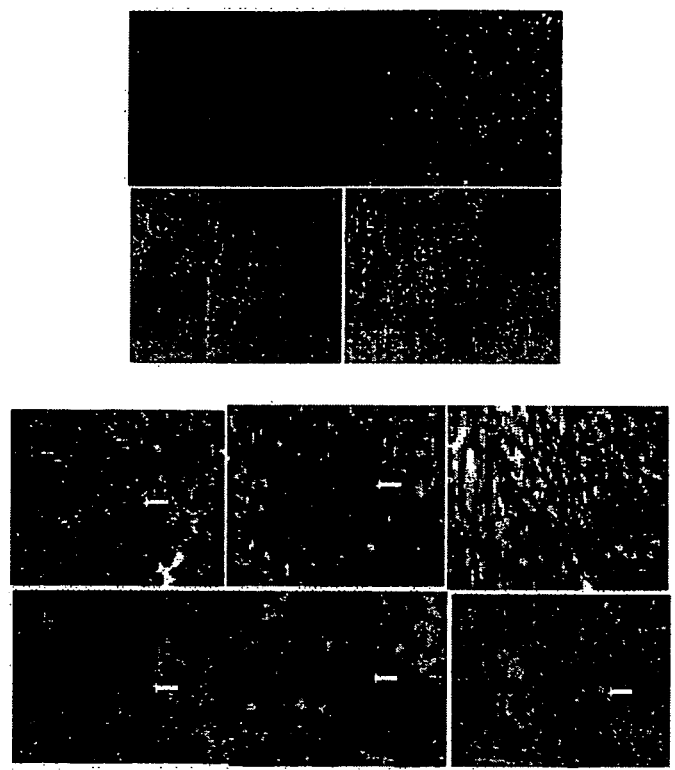
FIG. 8 depicts the in vitro characterization of C-PDLSCs. (A and B) Alizarin red staining showed mineralized nodule formation (A). In the regular culture conditions, the C-PDLSCs were not able to form mineralized nodules (B). (C and D) C-PDLSCs were able to form oil red 0 positive lipid clusters (C). Regular culture medium could not induce any oil red 0 positive lipid clusters in C-PDLSCs (D). (E) When PDLSCs were cultured with 10 ng/ml TGFβ1 for four weeks, they formed distinct collagen fibers in vitro (open arrows). (F) The in vitro generated fibers were positive for anti-type I collagen antibody staining (open arrows). (G) In contrast, DPSCs were not able to form collagen fibers in vitro under the same culture conditions. (H) C-PDLSCs were also able to generate collagen aggregates in vitro when cultured with 10 ng/ml TGFβ1 for four weeks. (I) The newly generated aggregates were positive for anti-type I collagen antibody staining. (J) Pre-immunoserum negative control for immunohistochemical staining of anti-type I collagen antibody.

To evaluate the capacity for multipotential differentiation in vitro, established secondary C-PDLSC cultures were supplemented with L-ascorbate-2-phosphate, dexamethasone, and inorganic phosphate in order to induce an osteogenic/cementogenic differentiation as previously described (Miura et al., 2003; and see above). The results demonstrated that alizarin red-positive nodules formed in the C-PDLSC cultures following four weeks of induction, indicating calcium accumulation in vitro (FIGS. 8A and 8B). Next, the potentiality of PDLSCs to develop into adipocytes was examined. In analogy to what has been previously demonstrated for adult DPSCs and PDLSCs, C-PDLSCs were also found to possess the potential to develop into oil red O-positive lipid-laden fat cells following five weeks of culture with an adipogenic inductive cocktail (FIGS. 8C and 8D).

As demonstrated above, transplanted human PDLSCs were able to form type I collagen-positive PDL-like tissue within the transplants and also TGFβ could induce collagen expression in BMSSCs. Whether TGFβ1 is able to up-regulate the expression of type I collagen, the main type of collagen present in PDL tissue, was also examined. Under the induction of TGFβ1, PDLSCs and C-PDLSCs produced aggregated type I collagen in culture, confirming their unique collagen-forming capacity (FIG. 8E-J). In contrast, DPSCs were not able to produce any collagen fibers under the same culture conditions (FIG. 8G).

Figure 9:
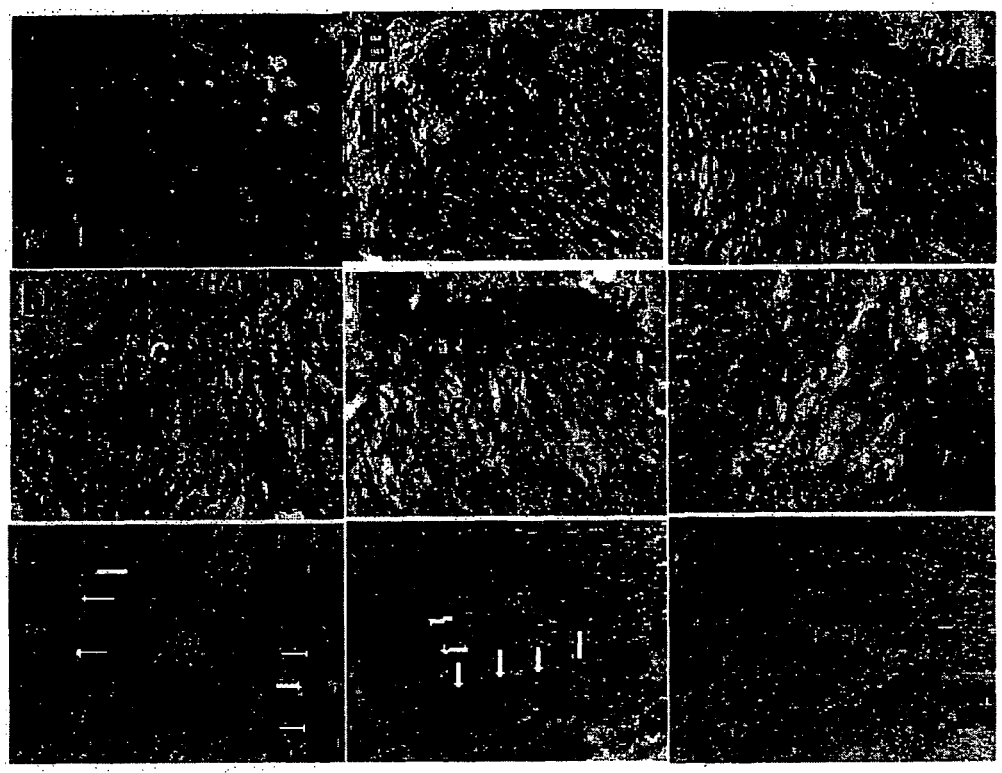
FIG. 9 depicts the in vivo characterization of C-PDLSCs. (A) After eight weeks of transplantation, C-PDLSCs were capable of forming a cementum-like structure (C) on the surfaces of the hydroxyapatite tricalcium (HA) carrier which was connected to PDL-like tissue (PDL). (B) The cells responsible for cementum (C) formation were positive for anti-human specific mitochondria antibody staining (black arrows). The immunohistochemical staining data indicated that transplanted C-PDLSCs differentiated into cementoblasts/cementocytes and generated cementum in vivo. (C and D) Transplanted C-PDLSCs were able to form cementum (C) on the surfaces of HA/TCP particles (HA) and were able to generate Sharpey's fibers (black arrows) inserted into cementum and which were continuous with PDL-like tissue (PDL), shown by H&E (C) and Trichrome staining (D). (E and F) Of 6 selected single-colony derived C-PDLSC strains, four (67%) were capable of generating a cementum/PDL-like structure (E). Newly formed cementum (C) was found to be adjacent to the surfaces of the HA/TCP carrier (HA) and was connected with PDL-like tissue (PDL) by Sharpey's fibers (black arrows). The remaining 33% (2 of 6) single-colony derived C-PDLSC strains were unable to generate cementum in vivo (F). (G and H) Newly formed cementum (C) was positive for anti-type I collagen antibody staining (G) and cementogenic cells were positive for anti-BSP antibody staining (open arrows in H). (I) Pre-immunoserum negative control for immunohistochemical staining of type I collagen and BSP antibodies.

It has been demonstrated that PDLSCs were able to form cementum/PDL-like tissues upon in vivo transplantation. To confirm the tissue regeneration capacity, C-PDLSCs were transplanted into immunocompromised mice subcutaneously using hydroxyapatite/tricalcium phosphate (HA/TCP) as a carrier. A typical cementum/PDL-like structure was generated in which a thin layer of cementum was formed on the surface of the HA/TCP and PDL-like structures associated with the newly regenerated cementum (FIG. 9A). The C-PDLSC transplants yielded human-specific mitochondria positive cementoblasts/cementocytes indicating in vivo differentiation of human C-PDLSCs (FIG. 9B). Moreover, collagen fibers inserted perpendicularly into cementum-like tissue (FIGS. 9C and 9D), mimicking the natural Sharpey's fibers in periodontal ligament. To gain a better understanding of in vivo differentiation of C-PDLSCs, 6 single colony strains of C-PDLSCs were selected and transplanted into immunocompromised mice as described above. Four out of six colonies could generate cementum and PDL structures with variable amounts of cementum/PDL fibers, while the remaining two colonies only showed fibrous tissue within the transplants (FIGS. 9E and 9F), suggesting that C-PDLSCs maintain heterogeneous characteristic of regular PDLSCs. Additionally, the regenerated cementum and cementoblasts were found to be positive for antitype I collagen and BSP antibody staining (FIG. 9G-I). These data confirmed that C-PDLSCs were capable of differentiating into cementoblasts and forming cementum in vivo.

To determine whether cryopreservation may influence the karyotype of cryopreserved PDLSCs, G-banded karyotype was performed to examine the chromosomal stability of C-PDLSCs. The C-PDLSCs exhibited a normal G-banded karyotype compared to the regular PDLSCs (data not show). These data suggest that C-PDLSCs may be usable for therapeutic purpose.

Figure 10:
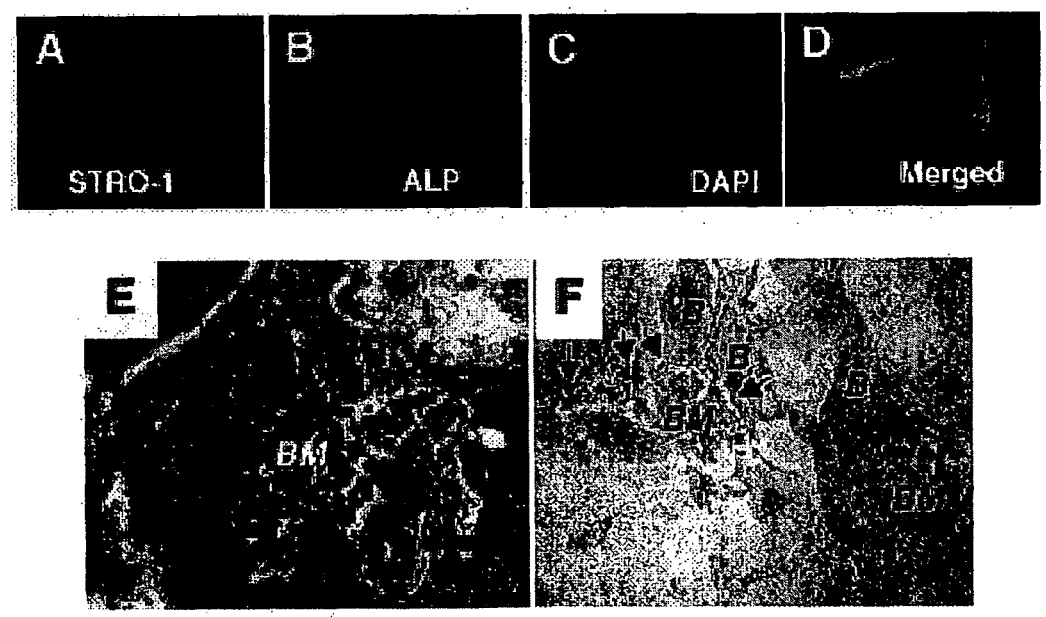
FIG. 10 demonstrates the retrieval of functional stem cells from cryopreserved human bone marrow stromal tissue. Colony forming cells can also be retrieved from frozen bone marrow stromal of facial bone chips as described in the methods. (A-D) BMSSCs derived from cryopreserved bone marrow stromal tissues attached on the bone chips, similar to regular BMSSCs, expressed STRO-1 and ALP in the culture. (E and F) After transplantation of BMSSCs derived from cryopreserved bone marrow stromal tissue, BMSSCs differentiated into osteoblasts (black arrows) and formed bone (B) and associated hematopoietic marrow elements (BM) as shown by H&E staining (E) and human specific Alu in situ hybridization (F).

To assess whether other cryopreserved tissue also contains postnatal stem cells, human BMSSCs were recovered from frozen-thawed bone marrow stromal tissue derived from bone chips. These recovered mesenchymal stem cells expressed stem cell marker STRO-1 and alkaline phosphotase (FIG. 10A-D). After expansion ex vivo, transplanted BMSSCs gave rise to a bone/marrow structure in vivo (FIG. 10E), similar to the regular BMSSC transplant. The BMSSCs differentiated into osteogenic cells as identified by human specific Alu in situ hybridization (FIG. 10F). These data indicated that functional postnatal stem cells could be retrieved from frozen tissues if they were cryopreserved according to the methods described herein.

Discussion

Previous experiments have shown that freshly isolated human PDL contains stem cells that are capable of differentiating into cementoblastic/osteoblastic cells in vitro and forming cementum/PDL-like tissues in vivo (described herein above). The present study demonstrates that human postnatal stem cells can be recovered from cryopreserved human PDL, thereby providing a practical clinical approach for the utilization of frozen tissues for stem cell isolation. Importantly, human C-PDLSCs maintain stem cell characteristics and in vivo tissue regeneration capacity, suggesting a great potential of using C-PDLSCs for periodontal tissue regeneration.

The rationale of isolating human postnatal stem cells from frozen tissues is to practically and effectively preserve clinical samples for subsequent stem cell recovery and potential stem-cell-mediated therapies. It is reasonable to speculate that cryopreservation of tissue in clinic will be much easier than isolation of stem cells that may require additional equipments and professional personnel. In this study, it was determined that C-PDLSCs are similar to the PDLSCs with respect to their STRO-1 positive characteristics. Therefore, C-PDLSCs may be derived from a population of perivascular cells (Gould et al., 1977; McCulloch, 1985). Moreover, C-PDLSCs show a heterogeneous nature that may reflect differences in their developmental stages or may even represent different PDL cell lineages analogous with non-frozen PDLSCs. This is emphasized in experiments where each colony-derived C-PDLSC clonal cell line showed a variable capacity to generate cementum, ranging from a total absence of any cementogenesis to levels comparable to multi-colony derived populations. It is notable that PDLSCs and C-PDLSCs were able to form collagen aggregates when cultured with TGFβ1 in vitro, reflecting a specificity of these stem cells to form collagen fibers for maintaining PDL tissue homeostasis. These data further support the notion that C-PDLSCs are functionally similar to PDLSCs.

Interestingly, hematopoietic progenitors can be recovered following cryopreservation of whole bone marrow in which individual cells were suspended within a liquid phase (Lundell et al., 1999). This is the first report/study to utilize frozen-thawed human tissue to isolate postnatal stem cells (that were previously identified as stem cells at a functional level). Although the recovered number of single colonies from six month frozen PDL was lower than PDLSCs derived from fresh PDL, there was no difference in terms of stem cell characteristics, including marker expression, proliferation rate, G-band karyotype, and in vivo tissue regeneration capacity. Additionally, there was no difference between the 3 and 6 months periods of frozen preservation with respect to the stem cell recovery rate, indicating that the duration of cryopreservation up to 6 months or more may not be injurious to the survival of C-PDLSCs.

The reason for the lower stem cell colony recovery rate is not known. There are many factors that can influence the viability of successfully cryopreserved stem cells including pre-freeze processing, variations in temperature and duration of storage, and post-freeze procedures (Hubel, 1997). The most common cause of the cell death is the intracellular ice formation during the freeze-thaw processing (Rowley et al., 2003; Woods et al., 2004). Cryopreservation can be improved to increase the post-thaw survival rate of cryopreserved stem cells by using, for example, trehalose, a nonreducting disaccharide of glucose (Eroglu et al., 2000; Guo et al., 2000).

Thus, postnatal stem cells can be recovered from human tissues. This is the first report that postnatal stem cells can be retrieved from solid frozen human tissue.

BIBLIOGRAPHY

Amar, S., Chung K. M. (1994) Clinical implications of cellular biologic advances in periodontal regeneration. Curr Opin Periodontal 128-40.

Bartold, P. M., McCulloch, Calif., Narayanan, A. S., Pitaru, S. (2000). Tissue engineering: a new paradigm for periodontal regeneration based on molecular and cell biology. Peridontol. 2000 24:253-69.

Baum B J, Mooney D J (2000). The impact of tissue engineering on dentistry. J Am Dent Assoc 131(3):309-18.

Beertsen, W., Mcculloch, C. A., Sodek, J. (1997) The periodontal ligament: a unique, multifunctional connective tissue. Periodontal 2000. 13:20-40.

Bianco, P., Robey, P. G. (2001). Stem cells in tissue engineering. Nature 414(6859):118-21.

Boyko, G. A., Melcher, A. H., Brunette, D. M. (1981) Formation of new periodontal ligament by periodontal ligament cells implanted in vivo after culture in vitro. A preliminary study of transplanted roots in the dog. J Periodontal Res. 16:73-88.

Broxmeyer, H. E., Srour, E. F., Hangoc, G., Cooper, S., Anderson, S. A., Bodine, D. M. (2003). High efficiency recovery of functional hematopoietic progenitor and stem cells from human cord blood cryopreserved for 15 years. Proc Natl Acad Sci USA. 100(2):645-50.

Brent, A. E., Schweitzer, R. Tabin, C. J. (2003) A somatic compartment of tendon progenitors. Cell. 113:235-48.

Cochran, D. I., Wozney, J. M. (1999) Biological mediators for periodontal regeneration. Periodontal 2000. 19:40-58.

Cochran, D. I., Jones, A., Heijl, L., Mellonig, J. T., Schoolfield, J., King, G. N. (2003) Periodontal regeneration with a combination of enamel matrix proteins and autogenous bone grafting. J Perdiodontal. 74:1269-81.

Cochran, D. I., King, G. N., Schoolfield, J., Velasquez-Plata, D., Mellonig, J. T., Jones, A. (2003) The effect of enamel matrix proteins on periodontal regeneration as determined by histological analyses. J Periodontal. 74:1043-55.

Desvarieux, M., Demmer, R. T., Rundek, T. et al. (2003) Relationship between periodontal disease, tooth loss, and cartotid artery plaque: the Oral Infections and Vascular Disease Epidemiology Study (INVEST). Stroke. 34:2120-25.

Elter, J. R., Offenbacher, S., Toole, J. F., Beck, J. D. (2003) Relationship of periodontal disease and edentulism to stroke/TIA. J Dent Res. 82:998-1001.

Eroglu, A., Russo, M. J., Bieganski, R., Fowler, A., Cheley, S., Bayley, H., Toner, M. (2000). Intracellular trehalose improves the survival of cryopreserved mammalian cells. Nat Biotechnol. 18(2):163-7.

Evers, B. M., Weissman, I. L., Flake, A. W., Tabar, V., Weisel, R. D. (2003). Stem cells in clinical practice. J Am Coll Surg. 197(3):458-78.

Guo, N., Puhlev, I., Brown, D. R., Mansbridge, J., Levine, F. (2000). Trehalose expression confers desiccation tolerance on human cells. Nat Biotechnol. 18(2):168-71.

Gould, T. R., Melcher, A. H., Brunette, D. M. (1980) Migration and division of progenitor cell populations in periodontal ligament after wounding. J. Periodontal Res. 15:20-42.

Gould, T. R., Melcher, A. H., Brunette, D. M. (1977) Location of progenitor cells in periodontal ligament of mouse molar stimulated by wounding. Anat Rec. 188:133-41.

Gronthos S, Brahim J, Li W, Fisher L W, Cherman N, Boyde A, DenBesten P, Robey P G, Shi S (2002). Stem cell properties of human dental pulp stem cells. J Dent Res 81(8):531-5.

Gronthos S, Mankani M, Brahim J, Robey P G, Shi S (2000). Postnatal human dental pulp stem cells (DPSCs) in vitro and in vivo. Proc Natl Acad Sci USA 97(25):13625-30.

Grzesik, W. J., Kuzentsov, S. A., Uzawa, K., Mankani, M., Robey, P. G., Yamauchi, M. (1998) Normal human cementum-derived cells: isolation, clonal expansion, and in vitro and in vivo characterization. J Bone Miner Res. 13:1547-54.

Grzesik, W. J., Narayanan, A. S. (2002) Cementum and periodontal wound healing and regeneration. Crit Rev Oral Biol Med. 13:474-84.

Han, X., Amar, S. (2003) IFG-1 signaling enhances cell survival in periodontal ligament fibroblasts vs. gingival fibroblasts. J Dent Res. 82:454-59.

Handa, K., Saito, M., Yamauchi, M., Kiyono, T., Sato, S., Teranaka, T., & Sampath Narayanan, A. (2002) Bone 31(5):606-611.

Handa, K., Saito, M., Tsunoda, A, et al. (2002) Progenitor cells from dental follicle are able to form cementum matrix in vivo. Connect Tissue Res. 43:406-08.

He, Z., Liu, H. C., Rosenwaks, Z. (2003). Cryopreservation of nuclear material as a potential method of fertility preservation. Fertil Steril. 79(2):347-54.

Hoffman, D. I., Zellman, G. L., Fair, C. C., Mayer, J. F., Zeitz, J. G., Gibbons, W. E., Turner, T. G., Jr. (2003). Cryopreserved embryos in the United States and their availability for research. Fertil Steril. 79(5): 1063-9.

Hubel, A. (1997). Parameters of cell freezing: implications for the cryopreservation of stem cells. Transfus Med Rev. 11(3):224-33.

Kaigler D, Mooney D (2001). Tissue engineering's impact on dentistry. J Dent Educ 65(5):456-62.

Isaka, J., Ohazama, A., Kobayashi, M. et al. (2001) Participation of periodontal ligament cells with regeneration of alveolar bone. J Periodontal 2001. 72:314-23.

Kettunen P, Karavanova I, Thesleff I (1998). Responsiveness of developing dental tissues to fibroblast growth factors: expression of splicing alternatives of FGFR1, -2, -3, and of FGFR4; and stimulation of cell proliferation by FGF-2, -4, -8, and -9. Dev Genet 22(4):374-85.

Korbling, M., Estrov, Z. (2003). Adult stem cells for tissue repair—a new therapeutic concept? N Engl J. Med. 349(6):570-82.

Krebsbach, P. H., Kuznetsov, S. A., Satomura, K., Emmons, R. V., Rowe, D. W., Robey, P. G. (1997). Bone formation in vivo: comparison of osteogenesis by transplanted mouse and human marrow stromal fibroblasts. Transplantation 63(8): 1059-69.

Kuznetsov, S. A., Krebsbach, P. H., Satomura, K., Kerr, J., Riminucci, M., Benayahu, D., Robey, P. G. (1997). Single-colony derived strains of human marrow stromal fibroblasts form bone after transplantation in vivo. J Bone Miner Res. 12(9):1335-47.

Lekic, P., Rojas, J., Birek C., Tenenbaum, H., McCulloch, C. A. G. (2001) Phenotypic comparison of periodontal ligament cells in vivo and in vitro. J. Periodont. Res. 36:71-79.

Liu, H. W., Yacobi, R., Savion, N., Narayanan, A. S., Pitaru, S. (1997) A collagenous cementum-derived attachment protein is a marker for progenitors of the mineralized tissue-forming cell lineage of the periodontal ligament. J Bone Miner Res. 12:1691-99.

Lundell, B. I., Mandalam, R. K., Smith, A. K. (1999). Clinical scale expansion of cryopreserved small volume whole bone marrow aspirates produces sufficient cells for clinical use. J Hematother. 8(2): 115-27.

MacNeil, R. I., Somerman, M. J. (1999) Development and regeneration of the periodontium: parallels and contrasts. Periodontal 2000. 19:8-20.

Marcopoulou, C. E., Vavouraki, H. N., Dereka, X. E., Vrotsos, I. A. (2003) Proliferative effect of growth factors TGF-beta 1, PDGF-BB and rhbmp-2 human gingival fibroblasts and periodontal ligament cells. J Int Acad Periodontal. 82:23-27.

McCulloch, C. A., Melcher, A. H. (1983) Cell density and cell generation in the periodontal ligament of mice. Am J Anat. 167:43-58.

McCulloch, C. A., Bordin, S. (1991) role of fibroblast subpopulations in periodontal physiology and pathology. J Periodontal Res. 26:144-54.

McCulloch, C. A. (1985) Progenitor cell populations in the periodontal ligament of mice. Anat Rec. 211:258-62.

Melcher, A. H. (1970) Repair of wounds in the periodontium of the rat. Influence of periodontal ligament on osteogenesis. Arch Oral Biol. 15:1183-204.

Miura, Masako, Gronthos, S., Zhao, M., Lu, B., Fisher, L. W., Gehron Robey, P., & Shi, S. (2003) SHED: Stem cells from human exfoliated deciduous teeth. PNAS 100(10):5807-5812.

Murakami, Y., Kojima, T., Nagasawa, T., Kobayashi, H., & Ishikawa, I. (2003) Novel isolation of alkaline phosphatase-positive subpopulation from periodontal ligament fibroblasts. J. Periodontal. 74(6):780-786.

Nevins, M., Camelo, M., Nevins, M. I., Schenk, R. K., Lynch, S. E. (2003) Periodontal regeneration in humans using recombinant human platelet-derived growth factor-BB (rhPDGF-BB) and allogenic bone. J Periodontal. 74:1282-92.

Ohno, S., Doi, T., Fujimoto, K. et al. (2002) RGD-CAP (betaig-h3) exerts a negative regulatory function on mineralization in the human periodontal ligament. J Dent Res. 81:822-25.

Ouyang, H., McCauley, L. K., Berry, J. E., D'Errico, J. A., Strayhorn, C. L., Somerman, M. J. (2000) Response of immortalized murine cementoblasts/periodontal ligament cells to parathyroid hormone and parathyroid hormone-related protein in vitro. Arch Oral Biol. 45:293-303.

Pitaru, S., Pritzki, A., Bar-Kana, I., Grosskopf, A., Savion, N., Narayanan, A. S. (2002) Bone morphogenetic protein 2 induces the expression of cementum attachment protein in human periodontal ligament clones. Connect Tissue Res. 43:257-64.

Ripamonti, U., Reddi, A. H. (1997) Tissue engineering, morphogenesis, and regeneration of the periodontal tissue by bone morphogenetic proteins. Crit Rev Oral Biol Med 8(2):154-63.

Rowley, S. D., Feng, Z., Chen, L., Holmberg, L., Heimfeld, S., MacLeod, B., Bensinger, W. I. (2003). A randomized phase III clinical trial of autologous blood stem cell transplantation comparing cryopreservation using dimethylsulfoxide vs dimethylsulfoxide with hydroxyethylstarch. Bone Marrow Transplant. 31(11):1043-51.

Saito, Yoshinori et al. (2002) A cell line with characteristics of the periodontal ligament fibroblasts is negatively regulated for mineralization and Runx2/Cbfa1/Osf2 activity, part of which can be overcome by bone morphogenetic protein-2. Journal of Cell Science 115:4191-4200.

Seo, B.-M., Miura, M., Gronthos, S., Bartold, P. M., Batouli, S., Brahim, J., Young, M., Robey, P. G., Wang, C.-Y., Shi, S. (2004). Investigation of multipotent postnatal stem cells form human periodontal ligament. Lancet. 364:149-155.

Shi S, Robey P G, Gronthos S (2001). Comparison of human dental pulp and bone marrow stromal stem cells by cDNA microarray analysis. Bone 29(6):532-9.

Shi, S., Gronthos, S. (2003) Perivascular niche of postnatal mesenchymal stem cells in human bone marrow and dental pulp. J Bone Miner Res. 18:696-704.

Shi, S., Gronthos, S., Chen, S., Reddi, A., Counter, C. M., Robey, P. G., Wang, C.-Y. (2002). Bone formation by human postnatal bone marrow stromal stem cells is enhanced by telomerase expression. Nature Biotechnology. 20(6):587-591.

Shimono, M., Ishikawa, T., Ishikawa, H. et al. (2003) Regulatory mechanisms of periodontal regeneration. Microsc Res Tech. 60:491-502.

Smith A J, Lesot, H, (2001). Induction and regulation of crown dentinogenesis: embryonic events as a template for dental tissue repair? Crit Rev Oral Biol Med 12(5):425-37.

Thesleff, I., Tummers, M. (2003) Stem cells and tissue engineering: Prospects for Regenerating Tissues in Dental Practice. Med Princ Pract 12(suppl 1):43-40.

Tsukamoto Y, Fukutani S, Shin-Ike T, Kubota T, Sato S, Suzuki Y, Mori M (1992). Mineralized nodule formation by cultures of human dental pulp-derived fibroblasts. Arch Oral Biol 37(12): 1045-55.

Morsczeck et al. (Publication date: 2003-08-14). Pluripotent embryonic-like stem cells derived from teeth and uses thereof. WO03066840.

Woods, E. J., Benson, J. D., Agca, Y., Critser, J. K. (2004). Fundamental cryobiology of reproductive cells and tissues. Cryobiology. 48(2): 146-56.

Young, H. E. (2004) Existence of reserve quiescent stem cells in adults, from amphibians to humans. Curr Top Microbiol Immunol 280:71-109.

Young, Henry E. et al. (2001) Clonogenic analysis reveals reserve stem cells in postnatal mammals: I. Pluripotent mesenchymal stem cells. The Anatomical Record 263:350-360.

Young, Henry E. et al. (2001) Human reserve pluripotent mesenchymal stem cells are present in the connective tissues of skeletal muscle and dermis derived from fetal, adult and geriatric donors. The Anatomical Record 264:51-52.

Zhao, M. Xiao, G., Berry, J. E., Franceschi, R. T., Reddi, A., Somerman, M. J. (2002) Bone morphogenetic protein 2 induces dental follicle cells to differentiate toward a cementoblast/osteoblast phenotype. J Bone Miner Res. 17:1441-51.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A composition consisting of an effective amount of an isolated clonal population of periodontal ligament multipotent mammalian stem cells wherein the clonal population consists of human multipotent stem cells that proliferate, express STRO-1 and MUC 18, form colonies in vitro, and differentiate into periodontal ligament cells that produce collagen fibers and cementum in vivo, wherein the periodontal ligament multipotent stem cells were expanded ex vivo and a biocompatible three dimensional carrier, wherein the carrier comprises a polymer, gelatin, polyvinyl sponges, a collagen matrix, or a combination of hydroxyapatite and tricalcium phosphate.

2. A method to generate periodontal tissue or cells in a subject comprising implanting the composition of claim 1 into tissue of the subject.

3. The method of claim 2, wherein the generated periodontal tissue comprises periodontal ligament, cementocytes, cementoblasts or cementum.

4. The method of claim 3, wherein the cementocytes or cementoblasts express bone sialoprotein (BSP), osteocalcin (OSC), matrix extracellular protein (MEPE), human mitochondrial protein or any combination thereof.

5. The method of claim 3, wherein the cementum expresses type I collagen and/or fibromodulin.

6. The method of claim 3, wherein the composition is implanted to reduce or ameliorate trauma within the subject.

7. The method of claim 6, wherein the trauma is periodontal disease.

8. The method of claim 6, wherein the trauma is a physical injury.

9. The method of claim 8, wherein the physical injury is due to a dental procedure.

10. The method of claim 2, wherein the composition is transplanted into periodontal tissue contained within the subject.

11. The method according claim 2, wherein the subject is human.

12. A composition consisting of an effective amount of an isolated clonal population of periodontal ligament multipotent mammalian stem cells wherein the clonal population consists of human multipotent stem cells that proliferate, express STRO-1 and MUC 18, form colonies in vitro, and differentiate into periodontal ligament cells that produce collagen fibers and cementum in vivo, wherein the periodontal ligament multipotent stem cells were expanded ex vivo, and wherein the isolated clonal population of periodontal ligament multipotent mammalian stem cells are in a carrier consisting of an effective amount of hydroxyapatite or tricalcium phosphate.

13. A method to generate periodontal tissue or cells in a subject comprising implanting the composition of claim 12 into tissue of the subject.

14. The method of claim 13, wherein the generated periodontal tissue comprises periodontal ligament, cementocytes, cementoblasts or cementum.

15. The method of claim 14, wherein the cementocytes or cementoblasts express bone sialoprotein (BSP), osteocalcin (OSC), matrix extracellular protein (MEPE), human mitochondrial protein or any combination thereof.

16. The method of claim 14, wherein the cementum expresses type I collagen and/or fibromodulin.

17. The method of claim 14, wherein the composition is implanted to reduce or ameliorate trauma within the subject.

18. The method of claim 17, wherein the trauma is periodontal disease.

19. The method of claim 17, wherein the trauma is a physical injury.

20. The method of claim 19, wherein the physical injury is due to a dental procedure.

21. The method of claim 13 wherein the composition is transplanted into periodontal tissue contained within the subject.

22. The method according claim 13, wherein the subject is human.

23. A composition consisting of a) an effective amount of a carrier consisting of a combination of hydroxyapatite and tricalcium phosphate, and b) an effective amount of an isolated clonal population of periodontal ligament multipotent mammalian stem cells, wherein the clonal population consists of human multipotent stem cells that proliferate, express STRO-1 and MUC 18, form colonies in vitro, and differentiate into periodontal ligament cells that produce collagen fibers and cementum in vivo, wherein the periodontal ligament multipotent stem cells were expanded ex vivo, wherein the human periodontal multipotent stem cells express STRO-1, MUC18, and scleraxis and wherein the isolated cells are in the carrier of a).

24. A method to generate periodontal tissue or cells in a subject comprising implanting the composition of claim 23 into tissue of the subject.

25. The method of claim 24, wherein the generated periodontal tissue comprises periodontal ligament, cementocytes, cementoblasts or cementum.

26. The method of claim 25, wherein the cementocytes or cementoblasts express bone sialoprotein (BSP), osteocalcin (OSC), matrix extracellular protein (MEPE), human mitochondrial protein or any combination thereof.

27. The method of claim 25, wherein the cementum expresses type I collagen and/or fibromodulin.

28. The method of claim 25, wherein the composition is implanted to reduce or ameliorate trauma within the subject.

29. The method of claim 28, wherein the trauma is periodontal disease.

30. The method of claim 28, wherein the trauma is a physical injury.

31. The method of claim 30, wherein the physical injury is due to a dental procedure.

32. The method of claim 24 wherein the composition is transplanted into periodontal tissue contained within the subject.

33. The method according claim 24, wherein the subject is human.

34. A composition consisting of a cryopreservative solution and an effective amount of an isolated clonal population of periodontal ligament multipotent mammalian stem cells wherein the clonal population consists of human multipotent stem cells that proliferate, express STRO-1 and MUC 18, form colonies in vitro, and differentiate into periodontal ligament cells that produce collagen fibers and cementum in vivo, wherein the periodontal ligament multipotent stem cells were expanded ex vivo, and wherein the isolated population is cryopreserved in the cryopreservative solution.

35. The composition of claim 34, wherein the composition has been cryopreserved in liquid nitrogen.

36. An isolated clonal population of periodontal ligament multipotent stem cells, wherein the clonal population consists of human multipotent stem cells that proliferate, express STRO-1 and MUC 18, form colonies in vitro, and differentiate into periodontal ligament cells that produce collagen fibers and cementum in vivo, wherein the periodontal ligament multipotent stem cells were expanded ex vivo, and wherein the periodontal ligament multipotent stem cells are transfected with a preselected nucleic acid segment and wherein the preselected nucleic acid segment encodes a hormone, a chemokine, a growth factor, growth factor receptor or a cytokine.

* * * * *